(12) United States Patent
Zhou et al.

(10) Patent No.: US 11,759,269 B2
(45) Date of Patent: *Sep. 19, 2023

(54) ENGAGEMENT AND/OR HOMING OF A SURGICAL TOOL IN A SURGICAL ROBOTIC SYSTEM

(71) Applicant: Verb Surgical Inc., Mountain View, CA (US)

(72) Inventors: Renbin Zhou, Mountain View, CA (US); Haoran Yu, Mountain View, CA (US); Sina Nia Kosari, Mountain View, CA (US)

(73) Assignee: Verb Surgical Inc., Santa Clara, CA (US)

( * ) Notice: Subject to any disclaimer, the term of this patent is extended or adjusted under 35 U.S.C. 154(b) by 718 days.

This patent is subject to a terminal disclaimer.

(21) Appl. No.: 16/661,590

(22) Filed: Oct. 23, 2019

(65) Prior Publication Data

US 2020/0054403 A1     Feb. 20, 2020

Related U.S. Application Data

(63) Continuation-in-part of application No. 15/999,561, filed on Aug. 20, 2018, now Pat. No. 11,406,457.

(51) Int. Cl.
*A61B 34/30* (2016.01)
*A61B 1/00* (2006.01)
(Continued)

(52) U.S. Cl.
CPC ............ *A61B 34/30* (2016.02); *A61B 1/0016* (2013.01); *A61B 1/00149* (2013.01);
(Continued)

(58) Field of Classification Search
CPC ... A61B 34/30; A61B 2034/305; A61B 34/32; A61B 34/37; A61B 34/70; A61B 34/71;
(Continued)

(56) References Cited

U.S. PATENT DOCUMENTS

| | | |
|---|---|---|
| 5,855,583 A | 1/1999 | Wang et al. |
| 6,102,850 A | 8/2000 | Wang et al. |

(Continued)

FOREIGN PATENT DOCUMENTS

| | | |
|---|---|---|
| CN | 102630154 B | 3/2015 |
| WO | WO2016201313 A1 | 12/2016 |
| WO | WO2019160865 A1 | 8/2019 |

OTHER PUBLICATIONS

International Search Report and the Written Opinion for International Patent Application PCT/US2019/058477 dated Jul. 17, 2020.

(Continued)

*Primary Examiner* — Ahmed M Farah
(74) *Attorney, Agent, or Firm* — Aikin & Gallant, LLP

(57) ABSTRACT

Engaging and/or homing is provided for a motor control of a surgical tool in a surgical robotic system. Where two or more motors are to control the same motion, the motors may be used to detect engagement even where no physical stop is provided. The motors operate in opposition to each other or in a way that does not attempt the same motion, resulting in one of the motors acting as a stop for the other motor in engagement. A change in motor operation then indicates the engagement. The known angles of engaged motors and the transmission linking the motor drives to the surgical tool indicate the home or current position of the surgical tool.

16 Claims, 12 Drawing Sheets

(51) Int. Cl.
*A61B 17/00* (2006.01)
*A61M 25/01* (2006.01)

(52) U.S. Cl.
CPC .............. *A61B 2017/003* (2013.01); *A61B 2017/00477* (2013.01); *A61B 2017/00725* (2013.01); *A61B 2034/301* (2016.02); *A61M 25/0113* (2013.01)

(58) Field of Classification Search
CPC .............. A61B 2034/715; A61B 17/00; A61B 2017/00398; A61B 2017/0042; A61B 2017/00477; B25J 17/02; B25J 17/0258; B25J 17/0266; B25J 17/0283; B25J 9/1612; B25J 9/1633; B25J 9/1651
USPC ........................... 606/1, 130; 901/2, 19, 36
See application file for complete search history.

(56) References Cited

U.S. PATENT DOCUMENTS

| | | | |
|---|---|---|---|
| 10,413,370 | B2 | 9/2019 | Yates et al. |
| 10,807,242 | B2 | 10/2020 | Zhou et al. |
| 11,071,441 | B2 | 7/2021 | Yu et al. |
| 11,406,457 | B2 * | 8/2022 | Yu ........................... B25J 17/02 |
| 11,426,246 | B2 * | 8/2022 | Asadian ................ A61B 34/77 |
| 2003/0125716 | A1 * | 7/2003 | Wang .................... B25J 9/1689 606/1 |
| 2006/0178559 | A1 * | 8/2006 | Kumar .................. G16H 40/63 600/109 |
| 2017/0020615 | A1 * | 1/2017 | Koenig .................. A61B 34/72 |
| 2017/0172549 | A1 | 6/2017 | Smaby |
| 2018/0085178 | A1 | 3/2018 | Komuro |
| 2018/0228559 | A1 | 8/2018 | Brierton |
| 2019/0059974 | A1 | 2/2019 | Shelton, IV et al. |
| 2019/0201137 | A1 | 7/2019 | Shelton, IV et al. |
| 2020/0054401 | A1 | 2/2020 | Yu et al. |
| 2021/0121257 | A1 * | 4/2021 | Yu .......................... A61B 34/70 |
| 2021/0321855 | A1 | 10/2021 | Yu et al. |

OTHER PUBLICATIONS

Non-Final Office Action for U.S. Appl. No. 15/999,561 dated Feb. 17, 2022, 5 pages.
Notice of Allowance for U.S. Appl. No. 15/999,561 dated Mar. 22, 2022, 10 pages.
International Search Report and Written Opinion for International Application No. PCT/US2019/058477 dated May 5, 2022, 8 pages.
U.S. Appl. No. 15/959,106, filed Apr. 20, 2018.
U.S. Appl. No. 15/999,561, filed Aug. 20, 2018.
Notice of Allowance for U.S. Appl. No. 15/999,561 dated Dec. 7, 2021, 9 pages.
International Preliminary Report on Patentability for International Application No. PCT/US2018/048812 dated Mar. 4, 2021, 9 pages.
International Search Report and Written Opinion for International Application No. PCT/US2018/048812 dated May 9, 2019, 13 pages.

* cited by examiner

ENGAGEMENT AND/OR HOMING OF A SURGICAL TOOL IN A SURGICAL ROBOTIC SYSTEM

RELATED CASE

This application is a continuation-in-part of prior application Ser. No. 15/999,561, filed Aug. 20, 2018, the disclosure of which is hereby incorporated by reference in its entirety

FIELD

Embodiments relate to control units for detecting the successful engagement and/or homing of a surgical robotic tool with one or more actuators in a surgical robotic arm of a surgical robotic system. Other embodiments are also described.

BACKGROUND

Surgical robotic systems give an operator or user, such as an operating surgeon, the ability to perform one or more actions of a surgical procedure using the surgical robotic system. In the surgical robotic system, a surgical tool or instrument, such as an endoscope, clamps, cutting tools, spreaders, needles, energy emitters, etc., is mechanically coupled to a robot joint of a surgical robotic arm, so that movement or actuation of the robot joint directly causes a rotation, pivoting, or linear movement of a part of the tool (e.g., rotation of an endoscope camera, pivoting of a grasper jaw, or translation of a needle). Once the tool is attached to (e.g., in contact with) a tool drive in the arm, operator commands may cause movements and activate functions of the attached tool, such as closing clamps, adjusting the bend of an endoscope, extending an instrument outside of cannula walls, applying pressure using a clamping tool, as well as other movements and actions.

Due to the varied nature of surgical procedures, different surgical tools or instruments may be selectively attached to the same arm of a surgical robotic system before and during a surgical procedure. In order to avoid equipment malfunctions during a surgical procedure, it is important that the surgical tool or instrument not only be attached to but also engaged in a mechanical sense to the robot joint of the surgical robotic arm. That is, mechanisms in the surgical tool that impart motion or enable the activation of instrument features (e.g., opening, closing, cutting, applying pressure, etc.), should be mechanically engaged to the actuators that are in the tool drive of the arm of the surgical robotic system, before the surgical tool is in use during the surgical procedure.

SUMMARY

By way of introduction, the preferred embodiments described below include methods, systems, instructions, and computer readable media for engaging and/or homing of a motor control of a surgical tool in a surgical robotic system. Where two or more motors are to control the same motion, the motors may be used to detect engagement even where no physical stop is provided. The motors operate in opposition to each other or in a way that does not attempt the same motion, resulting in one of the motors acting as a stop for the other motor in engagement. A change in motor operation then indicates the engagement. The known angles of engaged motors and the transmission linking the motor drives to the surgical tool indicate the home or current position of the surgical tool.

In a first aspect, a method is provided for engaging motor control of a surgical tool in a surgical robotic system. First and second motors connected with first and second drive discs, respectively, are rotated. The first and second drive discs are in contact with first and second tool discs. Both the first and second tool discs are linked to the surgical tool. The first and second motors rotate such that the first and second drive discs rotate in opposition to each other for movement of the surgical tool. Engagement of the first and second motors with the first and second discs, respectively, is detected from a change in performance of the first and second motors.

In a second aspect, a surgical robotic system is provided for engagement of motor control in a robotic surgery system. A surgical tool connects by a transmission to first and second rotary tool pads. The surgical tool connects such that rotation of the first and second rotary tool pads rotates the surgical tool. A tool drive has first and second rotary drives mateable with the first and second rotary tool pads. A processor is configured to detect mating of the first and second rotary tool pads with the first and second rotary drives by a change in a signal.

In a third aspect, a method is provided for homing a rotational position of a surgical tool in a surgical robotic system. Engagement of first and second rotary tool pads with first and second rotary drives is detected. A rotation angle of the surgical tool linked to the first and second rotary tool pads is determined from first and second rotation angles of the first and second rotary drives once the engagement is detected.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Embodiments of an apparatus, system and method for detection of engagement of a detachable surgical robotic tool to a tool drive of a surgical robotic arm of a surgical robotic system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics such as those shown in different drawings may be combined in any suitable manner in one or more embodiments.

Figure 1:
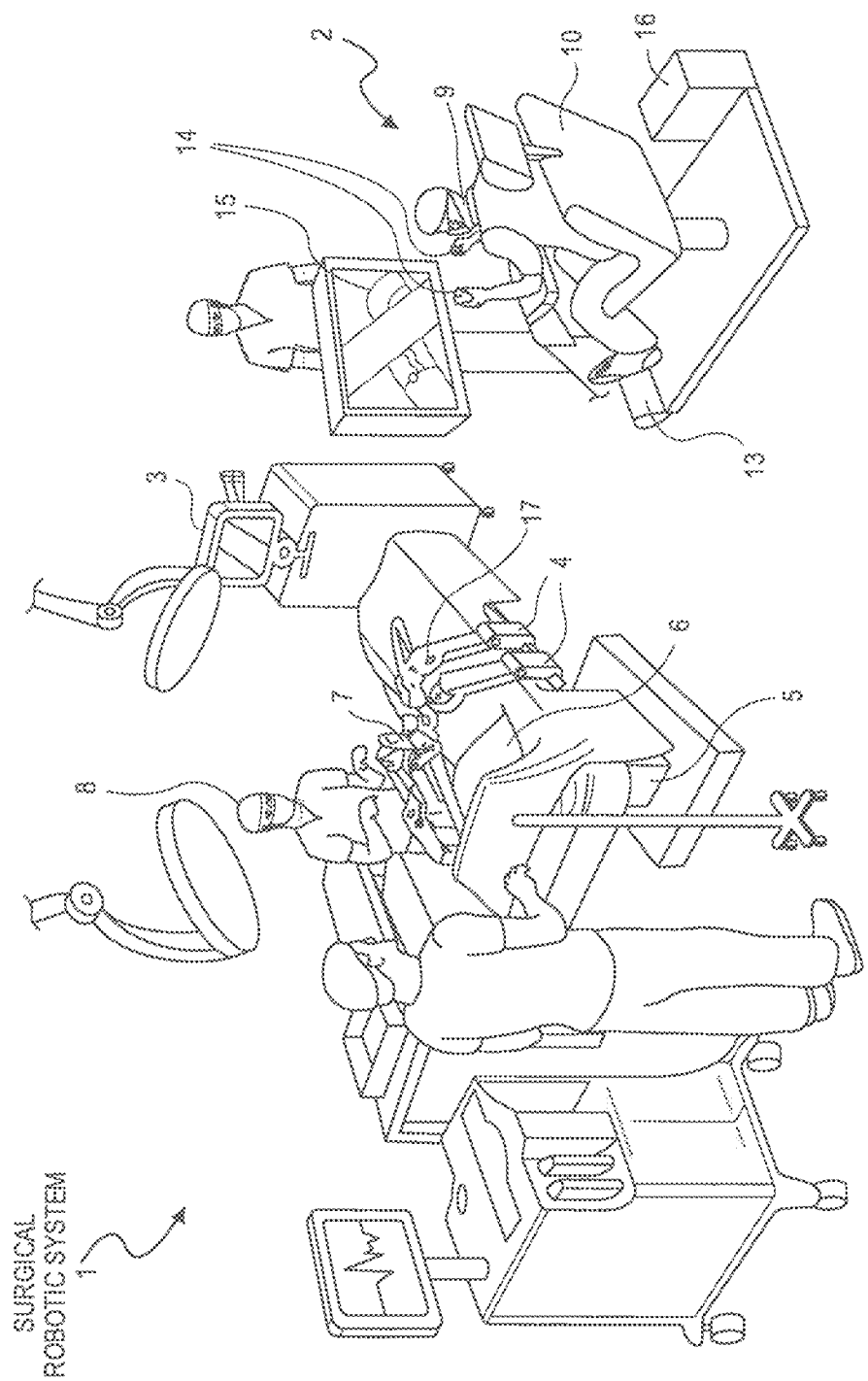
FIG. 1 is a pictorial view of an example surgical robotic system in an operating arena.

Referring to FIG. 1, this is a pictorial view of an example surgical robotic system 100 in an operating arena. The surgical robotic system 100 includes a user console 102, a control tower 103, and one or more surgical robotic arms 104 at a surgical platform 105, e.g., a table, a bed, etc. The surgical robotic system 100 can incorporate any number of devices, tools, or accessories used to perform surgery on a patient 106. For example, the surgical robotic system 100 may include one or more surgical tools 107 used to perform surgery. The surgical tool 107 may have an end effector at its distal end (also a distal end of the robotic surgical arm 4 to which the surgical tool 107 is attached), for executing a surgical operation such as cutting, grasping, poking, or energy emission.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 106 is a grasper that can grasp tissue of the patient. The surgical tool 106 may be controlled manually, directly by a hand of a bedside operator 108; or it may be controlled robotically, via sending electronic commands to actuate movement of the surgical robotic arm 104 to which the surgical tool 106 is attached. The surgical robotic arms 104 are shown as a table-mounted system, but in other configurations the surgical robotic arms 104 may be mounted in a cart, ceiling or sidewall, or in another suitable structural support.

Generally, a remote operator 109 such as a surgeon may use the user console 102 to remotely manipulate the surgical robotic arms 104 and the attached surgical tools 107, e.g., teleoperation. The user console 102 may be located in the same operating room as the rest of the surgical robotic system 100, as shown in FIG. 1. In other environments however, the user console 102 may be located in an adjacent or nearby room, or it may be at a remote location, e.g., in a different building, city, or country. The user console 102 may comprise a seat 110, foot-operated controls 113, one or more handheld user interface devices, UID 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the surgical robotic arms 104 and the surgical tools 107 (that are mounted on the distal ends of the surgical arms).

In some variations, the bedside operator 108 may also operate the surgical robotic system 100 in an "over the bed" mode, in which the beside operator 108 (user) is now at a side of the patient 106 and is simultaneously manipulating i) a robotically-driven tool (having an end effector) that is attached to the surgical robotic arm 104, e.g., with a handheld UID 114 held in one hand, and ii) a manual laparoscopic tool. For example, the bedside operator's left hand may be manipulating the handheld UID to control a surgical robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the surgical robotic system 100 are in a stowed configuration or withdrawn configuration (to facilitate access to the surgical site.) Once access is completed, initial positioning or preparation of the surgical robotic system 100 including its surgical robotic arms 104 may be performed. Next, the surgery proceeds with the remote operator 109 at the user console 102 utilizing the foot-operated controls 113 and the UIDs 114 to manipulate the various end effectors and perhaps an imaging system to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the surgical robotic arms 104. Non-sterile personnel may also be present to assist the remote operator 109 at the user console 102. When the procedure or surgery is completed, the surgical robotic system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the surgical robotic system 100. The UID 114 may be communicatively coupled to the rest of the surgical robotic system 100, e.g., via a console computer system 116. The UID 114 can generate spatial state signals corresponding to movement of the UID 114, e.g. position and orientation of the handheld housing of the UID, and the spatial state signals may be input signals to control a motion of the robot arm actuator 117. The surgical robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment of the surgical robotic arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

Surgical robotic system 100 may include several UIDs 114, where respective control signals are generated for each UID that control the actuators and the surgical tool (end effector) of a respective surgical robotic arm 104. For example, the remote operator 109 may move a first UID 114 to control the motion of an actuator 117 that is in a left robotic arm, where the actuator responds by moving linkages, gears, etc., in that surgical robotic arm 104. Similarly, movement of a second UID 114 by the remote operator 109 controls the motion of another actuator 117, which in turn moves other linkages, gears, etc., of the surgical robotic system 100. The surgical robotic system 100 may include a right surgical robotic arm 104 that is secured to the bed or table to the right side of the patient, and a left surgical robotic arm 104 that is at the left side of the patient. An actuator 117 may include one or more motors that are controlled so that they drive the rotation of a joint of the surgical robotic arm 104, to for example change, relative to the patient, an orientation of an endoscope or a grasper of the surgical tool 107 that is attached to that arm. Motion of several actuators 117 in the same surgical robotic arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the surgical platform 105 and the user console 102 may be through a control tower 103, which may translate user commands that are received from the user console 102 (and more particularly from the console computer system 116) into robotic control commands that are transmitted to the surgical robotic arms 104 on the surgical platform 105. The control tower 103 may also transmit status and feedback from the surgical platform 105 back to the user console 102. The communication connections between the surgical platform 105, the user console 102, and the control tower 103 may be via wired and/or wireless links, using any suitable ones of a variety of data communication protocols. Any wired connections may be optionally built into the floor and/or walls or ceiling of the operating room. The surgical robotic system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
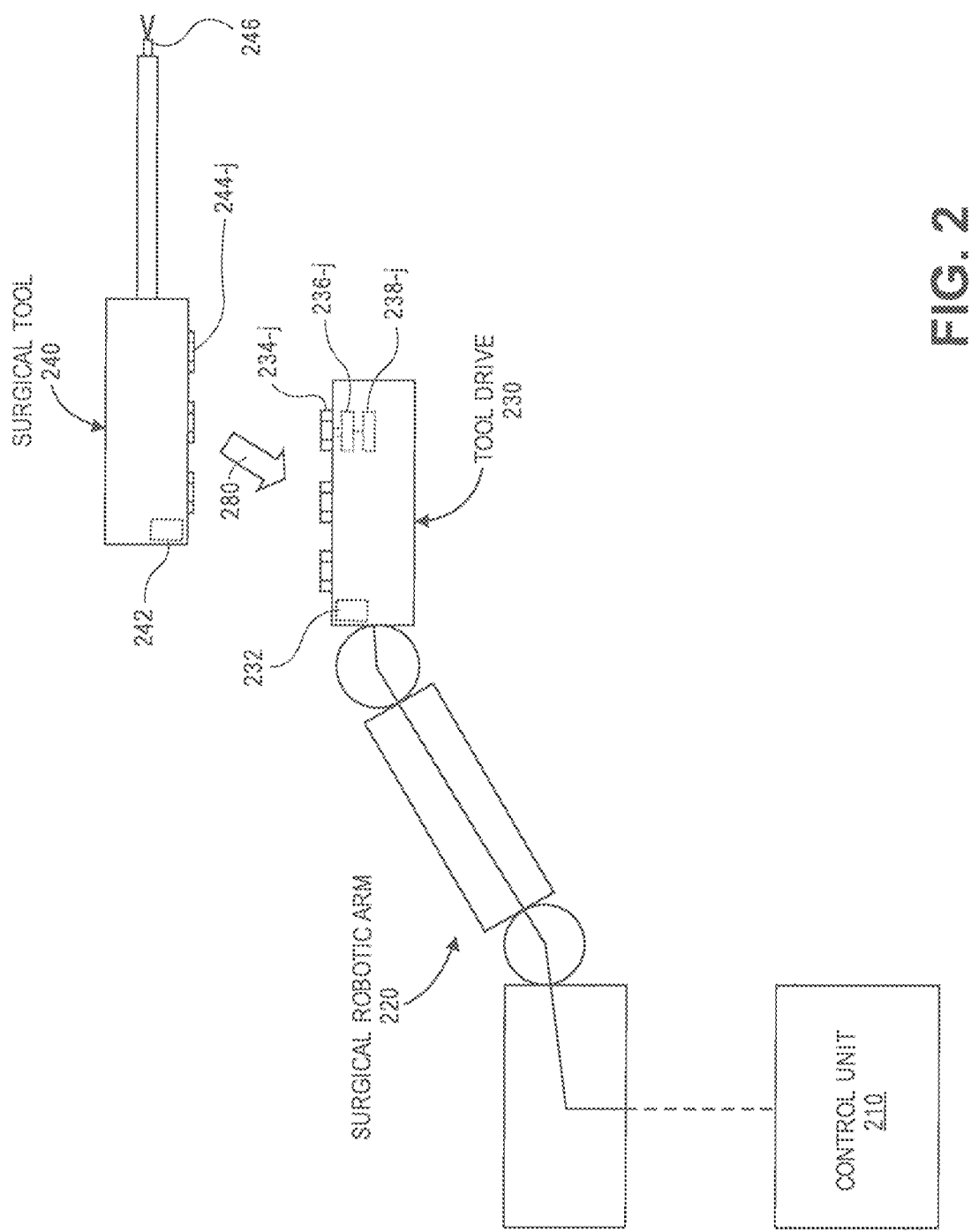
FIG. 2 is an illustration of a system for detecting engagement of a surgical tool to a tool drive of a surgical robotic arm.

FIG. 2 is an illustration of a subsystem or a part of the surgical robotic system 100, for detecting engagement of a surgical tool 240 to a tool drive 230 of a surgical robotic arm 220. The surgical robotic arm 220 may be one of the surgical robotic arms 104 of surgical robotic system 100 illustrated and discussed with respect to FIG. 1. The control unit 201 may be part of for example the control tower in FIG. 1. As discussed in more detail herein, the engagement may be detected by control unit 210 based on one or more motor operating parameters of one or more actuators (e.g., actuator 238-$j$) in the tool drive 230.

There is a tool drive 230 to which different surgical tools (e.g., surgical tool 240, as well as other detachable surgical tools—not shown) may be selectively attached (one at a time.) This may be done by for example a human user holding the housing of the surgical tool 240 in her hand and moving the latter in the direction of arrow 280 shown until the outside surface of the surgical tool 240 in which there are one or more tool disks (e.g., tool disk 244-$i$) comes into contact with the outside surface of the tool drive 230 in which there are one or more drive disks (e.g., drive disk 234-$j$). In the example shown, the tool drive 230 is a segment of the surgical robotic arm 220 at a distal end portion of the surgical robotic arm 220. A proximal end portion of the arm 220 is secured to a surgical robotic platform, such as a surgical table that is not shown in FIG. 2 but an example of which may be seen in FIG. 1 described above.

Control unit 210 is responsible for controlling motion of the various motorized joints in the surgical robotic arm 220 (including the drive disks 234) through which operation of end effector 246 (its position and orientation as well as its surgical function) which mimics that of a user input device is achieved. This is achieved via a mechanical transmission in the surgical tool 240, when the surgical tool 240 has been engaged to transfer force or torque from the tool drive 230. The control unit 210 may be implemented as a programmed processor, for example as part of the control tower 103 of FIG. 1. It may respond to one or more user commands received via a local or remote user input (e.g., joystick, touch control, wearable device, or other user input device communicating via console computer system 116.) Alternatively, the control unit 210 may respond to one or more autonomous commands or controls (e.g., received form a trained surgical machine learning model that is being executed by the control unit 210 or by the console computer system 116), or a combination thereof. The commands dictate the movement of robotic arm 220 and operation of its attached end effector 246.

The end effector 246 may be any surgical instrument, such as jaws, a cutting tool, an endoscope, spreader, implant tool, etc. Different surgical tools each having different end effectors can be selectively attached (one at a time) to robotic arm 220 for use during a surgical or other medical procedure. The end effector 246 depicted in the example of FIG. 2 is jaws located at a distal end of the surgical tool 240 and that may be retracted into, or extend out of, a cannula as shown (e.g., a thin tube that may be inserted into a patient undergoing a surgical procedure).

The robotic arm 220 includes a tool drive 230, in which there are one or more actuators, such as actuator 238-$j$. Each actuator may be a linear or rotary actuator that has one or more respective electric motors (e.g., a brushless permanent magnet dc motor) whose drive shaft may be coupled to a respective drive disk 234-$j$ through a transmission (e.g., a gear train that achieves a given gear reduction ratio—not shown). The tool drive 230 includes one or more drive disks 234 that may be arranged on a planar or flat surface of the tool drive 230, wherein the figure shows several such drive disks that are arranged on the same plane of the flat surface.

Each drive disk (e.g., drive disk 234-j) is exposed on the outside surface of the tool drive 230 and is designed to mechanically engage (e.g., to securely fasten via snap, friction, or other mating features) a mating tool disk 244-j of the surgical tool 240, to enable direct torque transfer between the two. This may take place once for example a planar or flat surface of the surgical tool 240 and corresponding or mating planar or flat surface of the tool drive 230 are brought in contact with one another.

Furthermore, a motor driver circuit (not shown but that may for example be installed in the tool drive 230 or elsewhere in the surgical robotic arm 220) is electrically coupled to the input drive terminals of a constituent motor of one or more of the actuators 238. The motor driver circuit manipulates the electrical power drawn by the motor in order to regulate for example the speed of the motor or its torque, in accordance with a motor driver circuit input, which can be set or controlled by control unit 210, which results in the powered rotation of the associated drive disk (e.g., drive disk 234-j).

When the mating drive disk 234-j is mechanically engaged to a respective tool disk 244-j, the powered rotation of the drive disk 234-j causes the tool disk 244-j to rotate, e.g., the two disks may rotate as one, thereby imparting motion on, for example, linkages, gears, cables, chains, or other transmission means within the surgical tool 240 for controlling the movement and operation of the end effector 246 which may be mechanically coupled to the transmission means.

Different surgical tools may have different numbers of tool disks based on the types of movements and the number of degrees of freedom in which the movements are performed by their end effectors, such as rotation, articulation, opening, closing, extension, retraction, applying pressure, etc.

Furthermore, within the surgical tool 240, more than one tool disk 244 may contribute to a single motion of the end effector 246 to achieve goals such as load sharing by two or more motors that are driving the mating drive disks 234, respectively.

In another aspect, within the tool drive 230, there may be two or more motors whose drive shafts are coupled (via a transmission) to rotate the same output shaft (or drive disk 234), to share a load.

In yet another aspect, within the surgical tool 240, there may be a transmission which translates torque from two drive disks 234 (via respective tool disks 244) for performing complimentary actions in the same degree of freedom, e.g., a first drive disk 234-i rotates a drum within the housing of the surgical tool 230 to take in one end of a cable, and a second drive disk 234-j rotates another drum within the housing of the surgical tool 230 to take in the other end of the cable. As another example, the extension and the shortening of an end effector along a single axis may be achieved using two tool disks 234-i, 234-j, one to perform the extension and another to perform the retraction, for example via different cables. This is in contrast to an effector that also moves in one degree of freedom (e.g., extension and shortening longitudinally along a single axis of movement) but that only needs a single tool disk to control its full range of movement. As another example, an effector that moves in multiple degrees of freedom (e.g., such as a wristed movement, movement along multiple axes, activation of an energy emitter in addition to end effector movement, etc.) may necessitate the use of several tool disks (each being engaged to a respective drive disk). In another type of surgical tool 240, a single tool disk 244 is sufficient to perform both extension and retraction motions, via direct input (e.g., gears). As another example, in the case of the end effector 246 being jaws, two or more tool disks 244 may cooperatively control the motion of the jaws, for load sharing, as discussed in greater detail herein.

In some embodiments, when surgical tool 240 is first attached to or installed on tool drive 230 such that the tool disks are brought substantially into coplanar and coaxial alignment with corresponding drive disks (though the tool and drive disks are perhaps not yet successfully engaged), control unit 210 initially detects the type of the surgical tool 240. In one embodiment, surgical tool 240 has an information storage unit 242, such as a solid state memory, RFID tag, bar code (including two-dimensional or matrix barcodes), etc., that identifies its tool or end effector information, such as one or more of identification of tool or end effector type, unique tool or end effector ID, number of tool disks used, location of those tool disks being used (e.g., from a total of six possible tool disks 244-e, f, g, h, i, j), type of transmission for the tool disks (e.g., direct drive, cable driven, etc.), what motion or actuation a tool disk imparts on the end effector, one or more tool calibration values (e.g., a rotational position of the tool disk as determined during factor testing/assembly of the tool), whether motion of the end effector is constrained by a maximum or minimum movement, as well as other tool attributes. In one embodiment, the information storage unit 242 identifies minimal information, such as a tool ID, which control unit 210 may use to perform a lookup of the various tool attributes.

The tool drive 230 may include a communication interface 232 (e.g., a memory writer, a near field communications, NFC, transceiver, RFID scanner, barcode reader, etc.) to read the information from the information storage unit 242 and pass the information to control unit 210. Furthermore, in some embodiments, there may be more than one information storage unit in surgical tool 240, such as one information storage unit associated with each tool disk 244. In this embodiment, tool drive 230 may also include a corresponding sensor for each possible information storage unit that would be present in a given tool.

Engagement

After surgical tool 240 is attached with tool drive 230, such that tool disks are brought into alignment and are superimposed on corresponding drive disks (although not necessarily mechanically engaged), and after the tool disk information is obtained, e.g., read by control unit 210, the control unit 210 performs an engagement process to detect when all of the tool disks that are expected to be attached to respective drive disks are mechanically engaged with their respective drive disks (e.g., their mechanical engagement has been achieved, or the tool drive is now deemed engaged with the tool). That is, attaching the surgical tool 240 with the tool drive 230 does not necessarily ensure the proper mating needed for mechanical engagement of tool disks with corresponding drive disks (e.g., due to misalignment of mating features). The engagement process may include activating one or more motors of an actuator (e.g., actuator 238-j) that drives a corresponding drive disk 234-j. Then, based on one or more monitored motor operating parameters of the actuator 238-j, while the latter is driving the drive disk 234-j, the mechanical engagement of the tool disk 244-i with a drive disk 234-j can be detected, as discussed in greater detail below. This process may be repeated for every drive disk 234 (of the tool drive 230) that is expected to be currently attached to a respective tool disk 244 (e.g., as determined based on the tool disk information obtained for the particular surgical tool 240 that is currently attached.)

Figure 3:
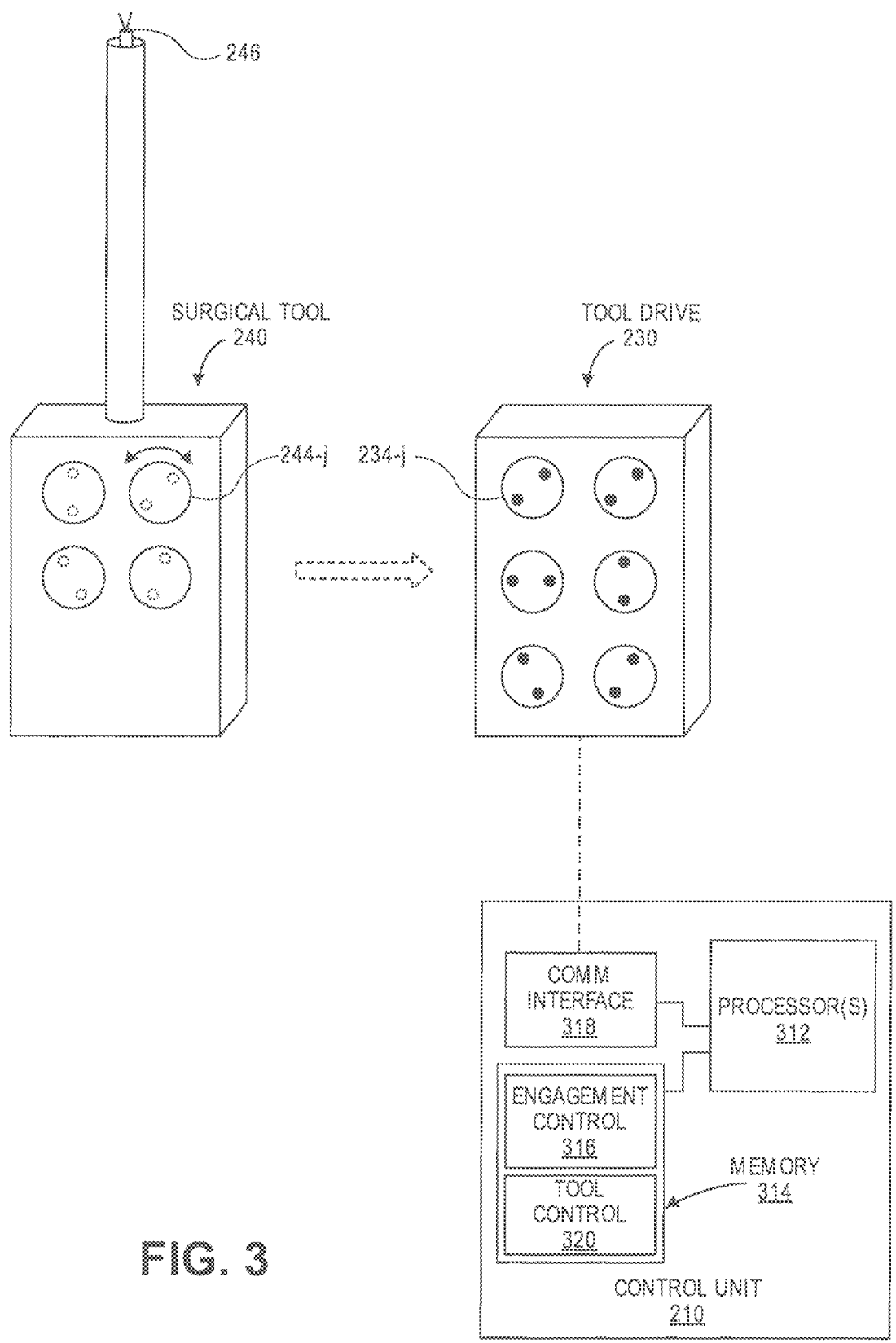
FIG. 3 is a block diagram showing a surgical tool, a tool drive, and a control unit.

Upon detecting that a particular type of surgical tool 240 has been attached with the tool drive 230, the control unit 210 activates one or more actuators (e.g., motors) of the tool drive 230 that have been previously associated with that type of surgical tool 240. In some embodiments, each actuator that is associated with a corresponding drive disk 234 of surgical tool 240 may be activated simultaneously, serially, or a combination of simultaneous and serial activation. FIG. 3 illustrates an example of the surgical tool 240 that utilizes four tool disks, such as tool disk 244-i, arranged in a coplanar fashion on a mating surface of its housing. Each tool disk contributes to at least a portion of the movement and/or activation of end effector 246. Upon detecting the attachment of surgical tool 240 with tool drive 230 (e.g., joining of mating surfaces of the respective housings), control unit 210 (or its processor 312 while executing instructions stored in memory 314 as engagement control 316) performs a process which determines that only the corresponding four drive disks, such as drive disk 234-j, need to be turned (a corresponding actuator 238-j needs to be activated—see FIG. 2) to perform the engagement process.

Returning to FIG. 2, during operation of actuator 238-j, after the detected attachment of surgical tool 240 with tool drive 230, one or more sensors 236-j measure one or more motor operating parameters of the actuator 238-j as its motor is signaled to start to move. In one embodiment, the actuator 238-j will turn in a direction that causes its attached (though not yet engaged) tool disk 244-i to wind a cable in the transmission housing of the tool 240, for cable driven surgical tools. As an example, see FIG. 4A in which motion 445 of the tool disk 244 avoids unwinding of cable 446, and thereby holds the tool disk 244 in place or starts to turn the tool disk 244 in the direction of motion 445 (which winds the cable 446.) This turning of the tool disk 244 continues until engagement is achieved as explained further below in connection with FIG. 4B and FIG. 4C.

In another embodiment, the selected actuator is signaled to turn so as to cause its attached tool disk 244 to rotate so that the end effector 246 that is connected to the tool disk 244 moves towards a physical constraint (e.g. a jaw opens until it stops against a cannula wall, a maximum in a range of motion is achieved when bumping against a hard stop in a fully open position, etc.) In yet another embodiment, such as an endoscope embodiment where two actuators are sharing the load being rotation of an endoscope camera where there may be no hard stops against rotation of the camera, the selected actuator rotates its attached tool disk 244-i in a direction that opposes the motion of another tool disk 244-j that is also rotatably coupled to the same output shaft in the transmission housing of the tool 240. In that instance, as soon as one of the tool disks 244-i, 244-j engages, it will act as a physical constraint to the other tool disk. Other predetermined directions of movement may also be used consistent with the discussion herein.

Furthermore, in some embodiments, the actuator's movement is ramped or increased gradually by the control unit 210 (e.g., the control unit 210 signals or commands the actuator to start to rotate at a slow speed at the beginning of movement and then progressively increase the speed, and then progressively decrease the speed at detection of engagement).

In one embodiment, the calibration values stored in the information storage unit 242 of the surgical tool 246 may be used to expedite tool engagement. For example, the calibration values can include a factory determined position (angle) of a particular tool disk 244-j, recorded during product assembly or testing. The engagement process may need to have knowledge of a home position of a corresponding drive disk 234-j. This knowledge may be obtained by the control unit 210 performing a tool driver calibration routine, in which it determines when a particular drive disk 234-j has reached a home position (as the control unit actuates the drive disk 234-j), such that position of that drive disk 234-j is now known by the control unit 210. Note that the control unit 210 may do so while only relying on output from a position sensor that is in the tool drive 230, and the tool 240 itself may be passive in that it has no electronic sensors in it.

Next, the control unit 210 may activate the corresponding actuator of the drive disk 234-j so that the drive disk 234-j turns at a high speed until a position variable of the drive disk 234-j comes close to the factory determined position. When the drive disk satisfies a threshold distance relative to the factory determined position (e.g., a home position of the tool disk) which implies that mating features of the tool disk and drive disk are near alignment, the speed may be reduced so as to increase the likelihood that the mating features will engage one another upon their initial encounter. This process may work for both direct transmissions as well as for tool disks that utilize a cable to drive the effector (as in FIG. 4A.) For the latter, the calibration value may include a rotation count (e.g., a number of complete rotations of a motor drive shaft) that can be used to limit the continued turning of the drive disk 234-j once engagement has been detected, to ensure that a maximum length of winding of the cable is not exceeded, or an angle of rotation of the engaged, tool disk 244-j and drive disk 234-j is not exceeded.

In some embodiments, the motor operating parameters monitored by the control unit 210 (via sensors 236) are interpreted to mean successful mechanical engagement of a tool disk with a drive disk. These can include measurements of torque applied by the actuator 238-j as measured by a torque or force sensor, measurements of current supplied to a motor of the actuator 238-j when attempting to drive the actuator to move at a certain velocity (e.g., where the sensor 236-j may include a current sensing resistor in series with a motor input drive terminal), measurements of electrical impedance as seen into the input drive terminals of the motor of the actuator when attempting to drive the motor to move at a certain velocity (e.g., where the sensor 236-j may also include a voltage sensing circuit to measure voltage of the motor input drive terminal), speed of the actuator 238-j (e.g., where the sensor 236-j may include a position encoder (sensor) on an output shaft of the actuator 238-j or on a drive shaft of the motor), as well as other parameters referred to here as motor operating parameters. While monitoring the one or more motor operating parameters of a particular actuator, when one or more of these parameters satisfies (e.g., meets or reaches) a predetermined, condition or threshold, the detection of such a situation can be interpreted by control unit 210 as a mechanical engagement event. Note that satisfying the predetermined condition may for example mean that the monitored operating parameter exhibits certain changes, as per the threshold, relative to an operating parameter of another motor that is part of the same actuator 238-j or that is part of another actuator 238-i which his being controlled by the control unit 210 simultaneously during the engagement detection process.

In some embodiments, detection of certain motor operating parameters during operation of the actuator 238-j, such as one or more of i) torque that satisfies (e.g., rises and reaches) a torque threshold, ii) motor current that satisfies (e.g., rises and reaches) a current threshold, iii) impedance that drops below an impedance threshold, iv) motor speed dropping below a motor velocity threshold, or a combination thereof, are used by control unit 210 to determine that mechanical engagement of tool disk 244-*j* to drive disk 234-*j* has occurred. The following are some examples of such a process.

Figure 4C:
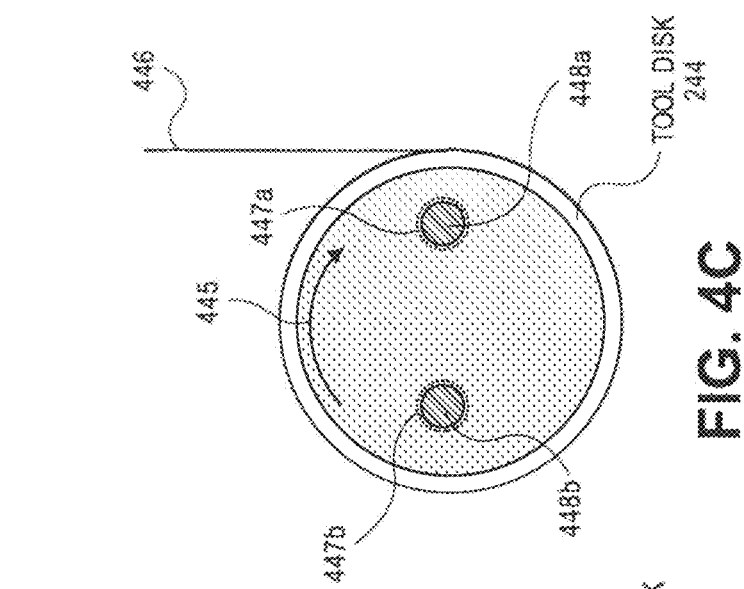
FIGS. 4A-4C illustrate different states of a tool disk and a drive disk during an engagement process.

In one embodiment, where the tool disk 244-*j* uses a cable 446 to control movement of its end effector 246, the actuator 238-*j* (that is driving the corresponding drive disk 234-*j*) will move in the direction that winds the cable (here, the direction of motion 445 of which the control unit 210 may have knowledge, based on having previously identified the type of tool 240). FIG. 4A depicts such a tool disk 244 that has a pair of coupling features 447*a*, 447*b* on its disk face, which are depicted as hollow circles. Each coupling feature 447*a*, 447*b* may be a separate, cylindrical cavity formed in the disk face. The direction of motion 445 will wind the cable 446 around it, where in this initial condition the cable 446 has some slack as shown that will disappear as the cable 446 is being wound in the direction of motion 445.

Figure 4B:
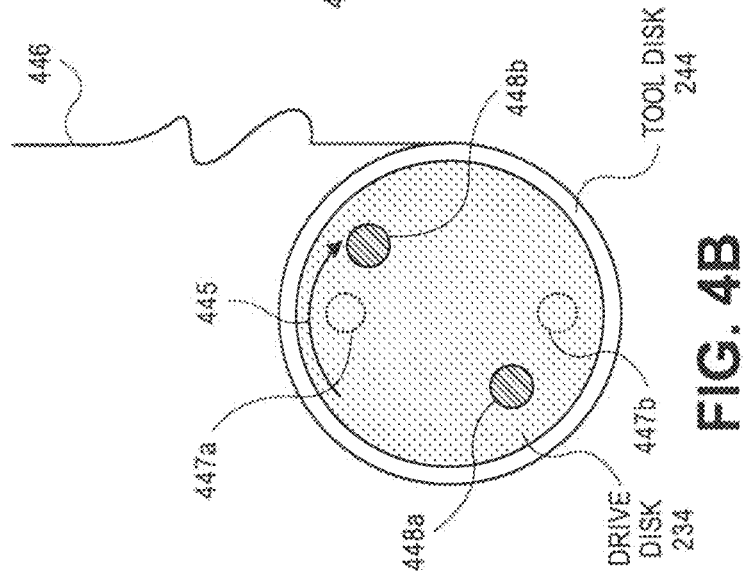
Figure 4A:
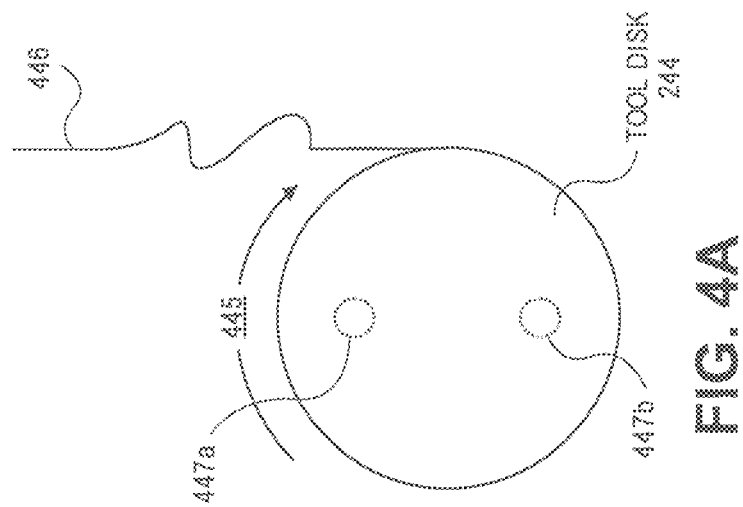

A drive disk 234 is concentrically aligned with the tool disk 244, as seen in FIG. 4B. That is, FIG. 4B illustrates drive disk 234 aligned and superimposed over the tool disk 244 such that their respective disk faces are brought into contact with one another. The drive disk 234 has a pair of coupling features 448*a*, 448*b* on its disk face, depicted as solid circles. Each coupling feature 448*a*, 448*b* may be a separate, cylindrical pin formed on the disk face. In this particular example, each of the coupling features 448 is sized to easily fit into either of the features 447 (once the two complementary features are aligned.) In FIG. 4B, the features 447*a*, 447*b* and the features 448*a*, 448*b* are misaligned even though the faces of their respective tool and drive disks are in contact with one another. In other words, in FIG. 4B one or more mating or complementary pairs of features, such as features 447*a*-448*a*, or features 447*a*-448*b*, are not yet mechanically engaged with each other. During such a condition, the drive disk 234 continues to be driven by its actuator 238, to move (turn) in the direction of movement 445 until mechanical engagement is reached in the condition depicted in FIG. 4C.

As illustrated in FIG. 4C, the drive disk 234 while turning has reached the point where both the coupling features 447*a*-448*a* and the coupling features 447*b*-448*b* have mechanically engaged each other as shown so that they now move as one (if the drive disk 234 continues to turn.) In the example here, each pin-cavity pair is now interlocked as shown in this figure. In addition, at this point the cable 446 is now taught after having been wound, and may thus serve to help hold the tool disk 244 in place (prevents its rotation) as drive disk 234 continues to turn in the direction of motion 445. Further turning of the drive disk 234 in the condition of FIG. 4C may increase tension in the cable 446 as the cable 446 pulls on its end effector 246 until a hard stop is reached which creates a physical constraint against further movement in the direction of movement 445 of the now-engaged drive disk 234.

The physical constraint on further turning of the drive disk 234 enables detection of the mechanical engagement event, by the control unit 210 making its measurement of motor operating parameters and comparison to one or more thresholds that may have been predetermined to be indicative of engagement. For example, the velocity/speed of the motor dropping below one or more threshold values indicates engagement because the motor is constrained from further movement in the winding direction. As another example, engagement occurs when the torque applied by the motor increases to a value greater than a freely moving motor and/or greater than the friction that results from tool disks and drive disks and/or attachment features rubbing or sliding against one another before engagement. Similarly, in other embodiments, the measured current and/or impedance approaches and may reach a maximum predetermined value when engagement occurs and as power is continued to be supplied to a motor in an attempt to continue movement of the drive disk in the predetermined direction. When one or more of these thresholds are satisfied, control unit 210 can conclude that engagement has occurred between a tool disk and a drive disk.

Other forms of physical constraint can be used by control unit 210 for detecting successful drive disk and tool disk engagement. For example, a motion constraint, such as a mechanical limit of a range of motion imposed by a joint of the end effector (e.g., a joint that can only rotate about an axis from −45 to 45 degrees) or a physical barrier to movement (e.g., a cannula wall that impedes movement of the end effector), may also be utilized as the physical constraint/hard stop discussed above for either cable driven or non-cable driven tools.

In some embodiments, the surgical tool 240 may not have a physical constraint/hard stop in at least one degree of freedom of movement from which motor operating parameters can be measured. For example, a tool disk 244-*j* may be responsible for imparting unconstrained rotation of the end effector 246 element about an axis. Even with such unconstrained movement however, the control unit 210 may still detect engagement of the drive disk 234-*j* to the tool disk 244-*j* by detecting changes in one or more motor operating parameters during the engagement detection process. For example, a motor operating parameter pattern, such as repeating torque spikes caused by the features 447 rotating past the features 488 (and thus not engaging each other) is indicative of lack of engagement. Accordingly, the stopping or non-existence of that torque spike pattern (while the drive disk 234-*j* continues to turn) means that the control unit 210 has detected tool disk to drive disk engagement.

In some embodiments, a physical constraint may be created by the use of coordinating movement of multiple drive disks, and/or by letting a single drive disk engage before engaging a second drive disk. For example, consider the case where two or more tool disks (in the same housing of a surgical tool 240) are connected by a transmission in the housing of the tool 240 to share a load (end effector 246) when turning in the same direction, such as when a cutting or clamping tool may need to apply force beyond that which a single actuator 238-*j* could supply. In such an embodiment, two or more actuators that are turning in the same direction (their respective drive disks are turning in the same direction) are driving the same output shaft that is inside the surgical tool 240 (due to the transmission in the surgical tool 240 that is connected to the corresponding tool disks.) Now, if the two actuators are signaled to move in opposing directions, then as soon as one of the drive disks engages its corresponding tool disk, this becomes a physical constraint to the other drive disk (when the other drive disk has engaged its corresponding tool disk.) When one of the two or more actuators engages (its drive disk engages its corresponding tool disk), the control unit 210 creates a constraint for the other actuator by signaling the engaged actuator to, for example, enter a position hold state. That is, a first actuator 238-*j* will be commanded by the control unit 210 to hold its position while the other, non-engaged actuator 238-*i* continues to be signaled to drive and thus turn or move (toward engagement between its drive disk 234-*i* and tool disk 244-*i*.) In this embodiment, one or both of the actuators' motor operating parameters can be monitored to detect engagement between a tool disk and drive disk pair. Furthermore, if a hard stop does exist (the control unit 210 expects or knows that this particular tool 240 has a hard stop), then the actuator of an engaged drive disk can be signaled to continue to drive or turn in the same direction until the hard stop is detected. The other actuator may continue to turn in the opposing direction and attempt to engage while the already engaged actuator holds its position at the hard stop.

Returning to FIG. 2, and as discussed above, the tool identification performed by control unit 210 enables the latter to get knowledge of the characteristics of the end effector 246 of surgical tool 240. For example, the control unit 210 may use that identification process to determine whether two (or more) tool disks in the tool 240 act in concert to impart end effector movement, whether one or more movements of the end effector are subject to hard stops or physical constraints, what are the ranges of movement of the end effector, what actuators will be used by the tool 240, and factory defined calibration values such as a home position of a tool disk. Note that a calibration value may encompass a range, e.g., 290 degrees+/−4 degrees. Based on such a calibration value, e.g., a home position of the tool disk 244-*i*, and based on the present position of the corresponding drive disk 234-*i* (determined using a position encoder in the tool drive 230), the control unit 210 can track the difference during the engagement process (as the actuator is signaled to turn.) So long as the difference is greater than a predetermined threshold, then the actuator is signaled to turn rapidly (fast rotation), and then in response to the difference becoming smaller than the threshold (implying that the drive disk is nearing the calibration value home position) the actuator is signaled to turn slowly (slow rotation). And that is expected to increase the chances of a reliable engagement being detected.

In some embodiments, after an engagement is detected by control unit 210, control unit 210 may take one or more additional actions with respect to the end effector 246 to confirm the engagement. For example, control unit 210 may subject the end effector to a predetermined set of one or more motions to test the engagement, such as signaling a drive disk to reverse direction thereby moving end effector in an opposite direction to what it was doing during the engagement process, moving the end effector to achieve an expected maximum degree of movement, etc. Such movements enable control unit 210 to for example reach a hard stop or reach a physical constraint again, which is detected as discussed herein based on one or more motor operating parameters, to confirm mechanical engagement between the tool disks and drive disks.

Furthermore, in some embodiments, control unit 210 may utilize the hard stop or physical constraint to set a reference position of the end effector. For example, knowing that a hard stop is to occur when the end effector reaches 270° of rotation in a certain direction, control unit 210 can set calibration values for a position of the corresponding actuator or drive disk. Then, movement of the actuator or drive disk can be tracked based on number of rotations of the drive disk, motor shaft, gear ratio, drive disk/motor indexing, etc.

Furthermore, in some embodiments, control unit 210 may signal actuation by one or more motors for a specified number of times, a specified number of rotations, or a combination thereof, when attempting to achieve engagement of tool disks with drive disks. When engagement is not achieved within a threshold amount of time, number of rotations, etc. control unit 210 may issue a warning to an operator of the surgical robotic system (e.g., an operator of system 100 of FIG. 1) to detach and then reattach surgical tool 240 to restart the engagement process.

After mechanical engagement of drive disks with tool disks is detected by control unit 210, an operator may command motions of one or more joints of surgical robotic arm 220. As discussed above, the commands are received from or originate from one or more UIDs (e.g., UID 114), as spatial state signals from the UIDs which are translated to corresponding control signals that the control unit 210 provides (e.g., a desired motor speed or current and direction of rotation) to energize one or more actuators of tool drive 230 which will change the pose, position or other state of the end effector. In one embodiment, where two or more actuators are cooperatively controlling the motion of the end effector, such as when two or more tool disks are to impart motion of the end effector in the same degree of freedom, control unit 210 further performs a cooperative control technique to ensure that the actuators operate in a complementary fashion when moving the end effector, share a load associated with movement of the end effector, do not fight one another in imparting such motion, maintain a balance between the actuators so that one actuator does not continually perform more or less work than the other actuators, etc. For example, when two or more actuators are used to control the opening, closing, and application of grip force of jaws of the end effector 246, control unit utilizes a multi-actuator operation control technique that identifies a first of the two or more actuators as a master actuator, and the remaining one or more actuators as slave actuators. Then, a position command that has been provided to signal the master actuator to move the end effector 246 to a commanded position, is also provided to signal the slave actuator to move the end effector 246 to the same commanded position. For instance, if the master actuator and the slave actuator are replicates, then if the master actuator receives a certain polarity (direction of rotation of its motor) and a certain motor current value to satisfy a given end effector position command, the same polarity and current value may also be supplied to each of the slave actuators. In some embodiments however, there may be some compensation for how motion of the actuators complement each other, for example, reversing polarity for the slaves when rotation directions of master and slave actuators are different, adjusting gain (e.g., of the commanded motor current) when attributes of the motors are different, etc., as discussed in greater detail herein.

FIG. 3 is a block diagram showing an example of the surgical tool 240, tool drive 230, and control unit 210. The surgical tool 240 may be attached with the tool drive 230 by bringing complementary or mating surfaces of their respective housings in contact within one another. The attaching may also include fastening the housings with one another. Furthermore, one or more sensors (not shown) of the tool drive 230 may be used by the control unit 210 to detect the attaching, including reading data from the surgical tool 240 that identifies the surgical tool 240, indicates which tool disks (e.g., tool disk 244-*j*) are used to control movements of the end effector 246, includes calibration values, indicates whether the tool has hard stops, or indicates which tool disks contribute to movement of or are connected by a transmission to other tool disks in the surgical 240. The data may be transferred to the control unit 210 via a communication link (e.g., a wired or wireless link) established between a communications interface 318 of the control unit 210 and sensor readout circuitry (not shown) in the tool drive 230. The data may then be stored in memory 314 as part of an engagement control program (engagement control 316) and may be associated with that particular surgical tool 240 so long as the latter remains attached to the tool drive 230.

The control unit 210 including its programmed processor 312 may be integrated into the surgical robotic system 100 (FIG. 1) for example as a shared microprocessor and program memory within the control tower 103. Alternatively, the control unit 210 may be implemented in a remote computer such as in a different room than the operating room, or in a different building than the operating arena shown in FIG. 1. Furthermore, control unit 210 may also include, although not illustrated, user interface hardware (e.g., keyboard, touch-screen, microphones, speakers) that may enable manual control of the robotic arm and its attached tool 240, a power device (e.g., a battery), as well as other components typically associated with electronic devices for controlling surgical robotic systems.

Memory 314 is coupled to one or more processors 312 (generically referred to here as "a processor" for simplicity) to store instructions for execution by the processors 312. In some embodiments, the memory is non-transitory, and may store one or more program modules, including a tool control 320 and an engagement control 316, whose instructions configure the processor 312 to perform the engagement processes described herein. In other words, the processor 312 may operate under the control of a program, routine, or the execution of instructions stored in the memory 314 as part of the tool control 320 and engagement control 316 to execute methods or processes in accordance with the aspects and features described herein.

In response to detecting the attaching of the surgical tool 240 with the tool drive 230, engagement control 316 performs (or rather configures the processor 312 to perform) a process for detecting the mechanical engagement of tool disks with corresponding drive disks (which are actuator driven), such as engagement of tool disk 344-$i$ with corresponding drive disk 334-$i$. The engagement control 316 may signal (through the tool control 320) that one or more of the actuators of tool drive 230 impart motion of their respective drive disks. In some embodiments, these instructions or signals include instructions to energize, activate or otherwise provide power to a motor so that the motor can produce or apply a specific amount of torque, cause the drive disk to rotate at a specific speed and direction, by applying a certain voltage command, current command, etc. Furthermore, the motion of each drive disk can be controlled to start rapidly initially during the engagement detection process, and then ramp down slowly once engagement is near, or proximity to alignment of mating features is detected or a predetermined time limit is reached without detecting engagement. For instance, based on the relative position of a drive disk to a tool disk (which may be based on a known calibration value), the actuator speed is ramped down to a predetermined speed (e.g., until the drive disk is within a threshold distance of where the mating features become aligned.

The engagement control 316 monitors one or more motor operating parameters of the motors of actuators of the tool drive 230. As discussed herein, the motor operating parameters can include torque imparted by a motor, voltage supplied to a motor, impedance as seen on the input drive terminals of a motor when attempting to drive the motor to move at a certain velocity, motor speed, as well as other motor operating parameters. One or more of these parameters may be monitored by comparing them to thresholds, so that when the thresholds are reached then a mechanical engagement event is deemed to have occurred (between, for example, tool disk 344-$i$ and drive disk 334-$i$.) As discussed herein, mechanical engagement is expected to be detected when corresponding mating features of a tool disk and a drive disk align and fasten with one another to that rotation of the drive disk will cause for example both immediate and proportional rotation of the mechanically engaged tool disk (as one with the drive disk.) Such engagement is expected to be detected when one or more of the motor operating parameters satisfies a threshold (e.g., reaching or exceeding a threshold indicative of a hard stop being reached, a maximum torque, voltage, or impedance value, a torque, voltage, or impedance value greater than what would be needed to overcome friction that initially appears when the tool 240 is first attached to the tool drive 230. The engagement control 316 thus infers or deduces that tool disk 344-$i$ and drive disk 334-$j$ have engaged with one another (e.g., fastening of respective disk mating features with one another).

Note that engagement control 316 need not monitor sensor readings for all of the motor parameters that are available from the tool drive 230. Instead engagement control 316 could monitor only one or more characteristics of interest based on, for example, whether surgical tool 240 is subject to any hard stops or physical movement constraints, whether one or more tool disks operate in concert (cooperate with each other) to impart movement on surgical tool 240, whether tool disks impart movement on surgical tool 240 via cables or directly (e.g., through a gear box), or a combination thereof, in order to determine when a threshold associated with engagement is satisfied.

In some embodiments, engagement control 316 monitors patterns of motor operating parameters, such as patterns of torque, voltage, motor speed, impedance, etc. that are the result of drive disk 234-$j$ rotating over tool disk 244-$j$ but without mechanical engagement. That is, a certain amount of torque, force, voltage, etc. could be measured, which is greater than what is exhibited by a free moving drive disk (where the surgical tool 240 is not attached to the tool drive 230) and less than a mechanically engaged drive disk (when for example mating features of the tool and drive disks pass each other while the tool and tool drive housings are in contact, but without engaging.) When this motor parameter pattern changes as detected, such as due to a hard stop or physical motion constraint being encountered, engagement control 316 is said to have detected mechanical engagement. Monitoring and interpreting pattern based motor operating pattern also enables engagement control 316 to detect engagement (between tool disk 344-$j$ and drive disk 334-$j$) even when no hard stop or motion constraint is available, or without having to drive a drive disk to a tool's hard stop or other motion constraint.

In some embodiments, when engagement control 316 detects mechanical engagement of tool disks with drive disks, it may also initiate a verification process or engagement check in which the actuators of tool drive 230 are signaled to undergo a predetermined set of one or more motions, to verify the detected engagement. For example, the actuators may be instructed to cause their respective drive disks to rotate in a direction opposite to the direction of engagement (the latter being the direction in which the drive disks were rotating when engagement was initially detected, e.g., in the direction of motion 445 seen in FIG. 4A). Then, the drive disks may be rotated back in the direction of engagement until a second engagement is detected (e.g., when a particular motor parameter reaches a threshold that is consistent with the tool disk reaching a hard stop or a motion constraint, when a particular motor parameter reaches a threshold that is consistent with resistance against the rotating tool disk that is not caused by friction alone (friction between the tool disk and a corresponding drive disk), or a combination thereof.

Engagement control 316, based on having detected engagement of tool disks to drive disks, or based on a countdown timer having expired without detecting engagement, generates a notification for an operator of the surgical robotic system. The notification may either indicate that engagement has occurred so that the surgical tool 240 is ready for use, or that engagement has not occurred and so the surgical tool 240 should be reattached.

Figure 5A:
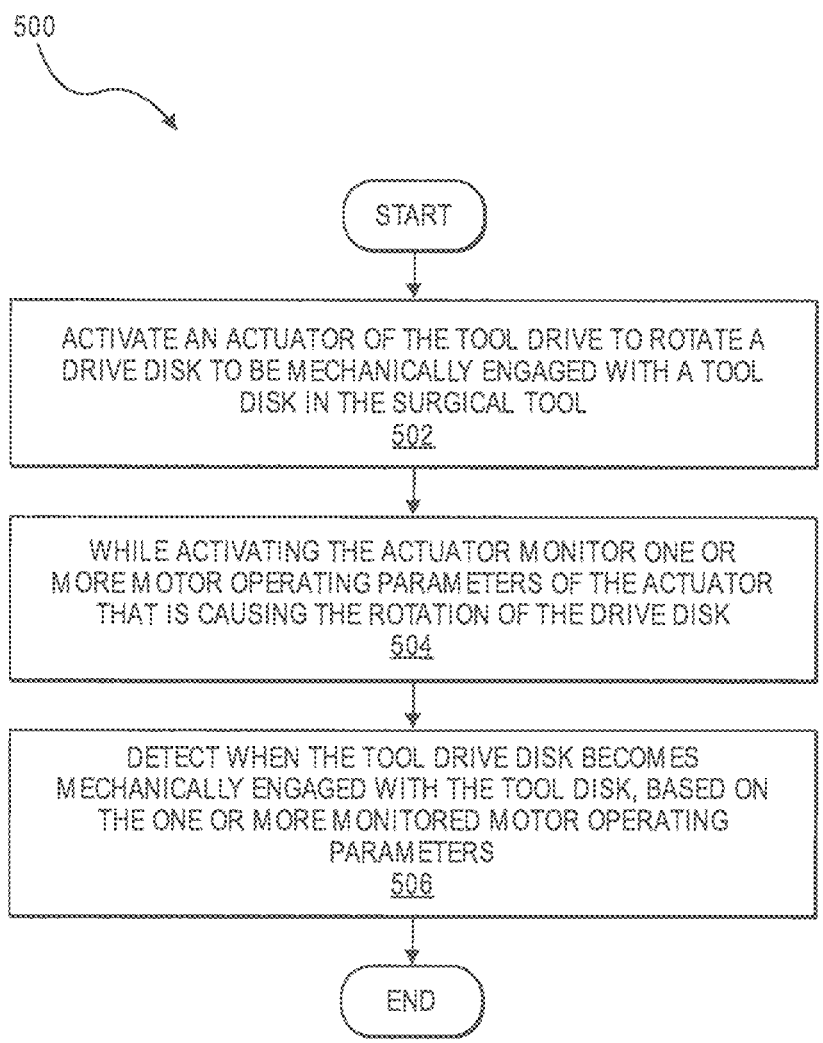
FIG. 5A is a flow diagram illustrating a process performed by a control unit for engaging a surgical tool with a tool drive.

FIG. 5A is a flow diagram illustrating a process 500 for engaging a surgical tool with a tool drive of a surgical robotic system, in accordance with an embodiment of the disclosure. The process 500 may be performed by a programmed processor (also referred to here as processing logic), configured according to software stored in memory (e.g., the processor 312 and the memory 314 of FIG. 3, where the processor 312 is configured according to the instructions of the tool control 320 and the engagement control 316.)

Referring to FIG. 5A, processing logic begins by activating an actuator of the tool drive to rotate a drive disk of the tool drive (processing block 502). For example, processing logic may activate a linear or rotary actuator of a tool drive (e.g., tool drive 230) to turn or rotate the drive disk (e.g., drive disk 234-*j*). Furthermore, as discussed herein, when mechanically engaged, the rotation of a drive disk (e.g., disk 234-*j*) will cause immediate or direct rotation of a corresponding tool disk (e.g., disk 244-*j*) of a surgical tool (e.g. surgical tool 240).

Processing logic monitors one or more motor operating parameters of the actuator that is causing the rotation of the drive disk while activating the motor (processing block 504). In some embodiments, the operating parameters of the motor being monitored can include torque, motor current, motor velocity, or a combination thereof.

Based on the one or more monitored motor operating parameters, processing logic detects when the drive disk becomes mechanically engaged with the tool disk (processing block 506). In one embodiment, the detection occurs when or in response to at least one of the one or more motor operating parameters being monitored satisfying a corresponding condition or threshold. For example, the condition can be associated with a value of a motor operating parameter that occurs in response to the motor reaching a physical constraint against further rotation of the tool disk (e.g., reaching a mechanical limit of a range of motion when a physical barrier to the movement is encountered, a maximum degree of movement of the end effector of the tool is reached, opposition with another activated motor actuator occurs, etc.). As another example, the condition may represent a motor operating parameter exhibited when there is friction due to the drive disk contacting and sliding against the tool disk during rotation but without the mechanical latching or fastening of the drive disk to the tool disk. In embodiments discussed herein, when mechanical engagement of the drive disk with the tool disk is detected, one or more additional actions, such as generating system or operator notifications, initiating one or more engagement verification operations, storing reference values, etc. may be performed by processing logic.

Figure 5B:
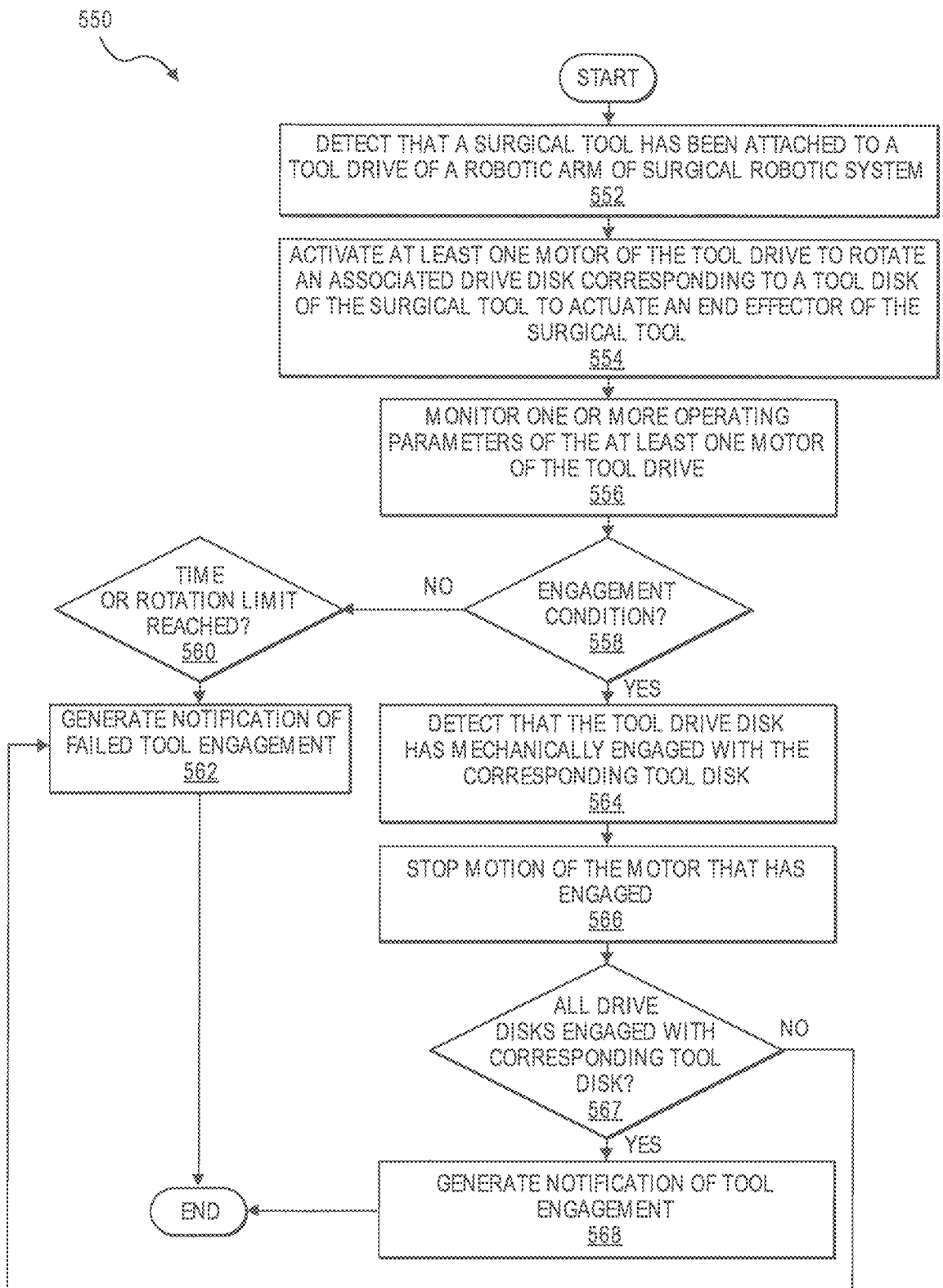
FIG. 5B is a flow diagram illustrating another process for a control unit detecting engagement of a tool disk to a drive disk based on one or more operating parameters of an actuator that is driving the drive disk.

FIG. 5B is a flow chart illustrating a process 550 for detecting engagement of a tool disk with a drive disk based on one or more motor operating parameters of an actuator that is driving the drive disk. The process 550 is performed by processing logic that may comprise any combination of hardwired circuitry and programmed processor, where for example the process 550 may be performed by the processor 312 programmed in accordance with the tool control 320 and engagement control 316 described above. The process may begin with detecting that a detachable surgical tool has been attached to a tool drive of a robotic arm of a surgical robotic system (processing block 552). The attachment may be detected based on sensors of the tool drive coming within wireless detection range or being conductively connected with an information storage unit in the detachable surgical tool. As discussed herein, the information storage unit may include a tool identifier, and may also include additional tool attributes, such as which of several available tool disks in the tool housing are actually connected by a transmission in the housing to the end effector in the detachable surgical tool, what type of transmission in the tool controls movement of the end effector (e.g., cable driven, direct drive, etc.), what direction of movement or rotation is allowed, if there are any ranges of such movement or rotation, calibration values (e.g., cable lengths, current cable length, maximum winding, rotational position of tool disks or a home position of a tool disk, etc.), as well as other tool attributes discussed herein.

At least one motor of the tool drive is then activated causing the at least one motor to rotate an associated drive disk corresponding to a tool disk (that is connected by a transmission in the surgical tool to control motion of the end effector (processing block 554). In one embodiment, a current to be supplied to the motor, a torque to be achieved by the motor, or a direction of movement is signaled to the tool control 320, so that the motor will cause the drive disk to rotate at a predetermined velocity in a predetermined direction. In other words, processing logic causes a signal to be sent to a motor driver circuit, commanding the motor driver circuit to apply power to or energize the motor. In some embodiments, the predetermined speed is set based on a determination, at the time of the detected attachment of the tool drive with the detachable surgical tool, of for example, the type of tool, tool drive transmission type (e.g., cable driven, direct drive, etc.), type of restraint that will be encountered (e.g., a hard stop, a physical constraint, opposing motion constraint), or a combination of such factors. One or more motor operating parameters of the at least one motor of the tool drive are then monitored (processing block 556). The monitored motor operating parameters may correspond with those being controlled by processing logic to cause motion of the motor (e.g., torque, speed.)

Returning to FIG. 5B, the processing logic repeatedly checks to see whether or not an engagement condition has been met, e.g., a monitored motor operating parameter has reached a threshold (processing block 558.) If so, then a mechanical engagement event is flagged, signifying that the drive disk has mechanically engaged with its corresponding tool disk (processing block 564). As discussed herein, the threshold is indicative of a condition associated with the mechanical engagement of the drive disks. For example, mechanical engagement is expected when the torque, current, or impedance associated with the motor at a predetermined velocity or speed exceeds their values that are associated the motor encountering tool drive to tool disk friction alone. The threshold may be a value which is greater than the torque, voltage, impedance, etc. needed to overcome such friction. As another example, movement of the end effector may be subject to a physical constraint, such as a maximum range of motion of a joint, a hard stop (e.g., as imposed by a cannula wall), an opposing motion of another drive disk, as well as other physical constraints. In that case, the speed and direction of movement of the motor are selected to advance the end effector or tool disk towards the physical constraint. Then, when the physical constraint is reached, the monitored torque, current, impedance will spike to a maximum, while the speed will drop to zero. In this example, one threshold may refer to torque or motor current that is set near its maximum value, and another threshold may refer to velocity that is set lower than a nominal speed of the motor during rotation of the drive disk, e.g., substantially zero. Thus, the two thresholds act as a check against one another to make the detection of engagement more robust.

In response to the detected engagement of the drive disk with the corresponding tool disk, the motion of the drive disk is stopped (processing block 566). In one embodiment, when the motion is stopped, one or more reference values associated with that position or state of the end effector may be stored for later reference and use. For example, where a physical constraint was used to detect the engagement, an index value of the motor, a rotation count, etc. at that moment can be stored, and used later for re-locating the end effector at or near the physical constraint. The physical constraint may be, e.g., maximum cable length, cannula wall, maximum of a range of motion, etc. Furthermore, to prevent excessive tensioning of a cable in the case of a cable driven tool, the motion of the drive disk may be stopped, or the motor deactivated, simultaneously or nearly simultaneously in response to the detection performed at block 558.

Once engagement of all of the relevant drive disks (those that correspond to in-use tool disks of the particular surgical tool) has been detected in processing block 567 (where the process described above in blocks 554-556-558-564-566 may have been performed for each respective drive disk) then a notification of tool engagement is then generated (processing block 568). The notification may be a visual notification (e.g., a graphical user interface notification), an audible notification (e.g., a tone, sound, etc.), sensory (e.g., a haptic notification), or a combination of such generated by user interface hardware of the surgical robotic system.

Returning briefly to processing block 558, when the engagement condition is not met (e.g., a monitored motor operating parameter does not satisfy a threshold such that mechanical engagement of a tool disk and a corresponding drive disk has not occurred), a determination of whether a time or rotation limit has been reached is performed (processing block 560). A failure to engage may be due to a broken cable, a tool disk and drive disk not positioned close enough to each other to allow for engagement, etc.) The time limit may be a predetermined maximum time interval (countdown timer value) in which a drive disk is allowed to rotate without detecting mechanical engagement with a tool disk. Similarly, the rotation limit may be a number of motor rotations necessary to impart one or more full rotations of its respective drive disk. For example, if the rotation limit is associated with one full rotation of the drive disk, it is assumed that engagement should occur within a single revolution of a drive disk. If the time limit, rotation limit, or some combination of limits are not reached (processing block 560), the monitoring of the one or more motor operating parameter values continues (return to processing block 556.) However, if the one or more limits are reached (processing block 560), a notification, similar to the notification of processing block 568, that an error has occurred and tool engagement has failed is generated (processing block 562). In this case, an operator of the surgical system may be instructed to detach the surgical tool from the tool drive, and then re-attach them to restart the engagement process of FIG. 5B.

Figure 5C:
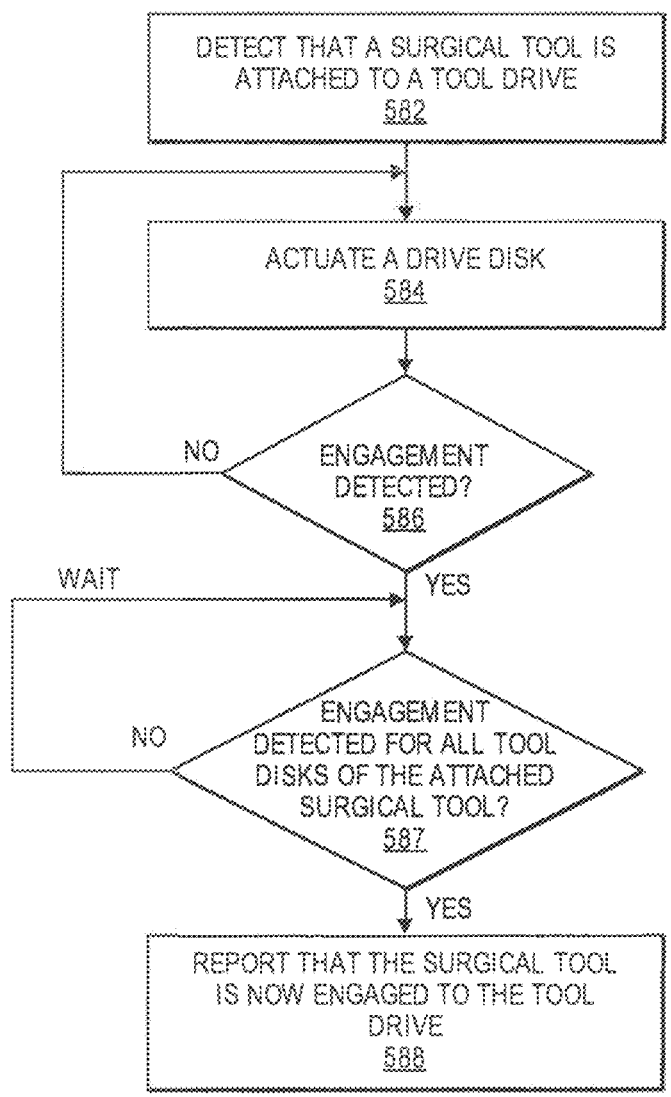
FIG. 5C is a flow diagram illustrating another process for a control unit to detect engagement of a surgical tool with a tool drive of a surgical robotic system.

Turning now to FIG. 5C, this is a diagram of a process performed by a control unit for engaging a surgical robotic tool with a tool drive, as part of a surgical robotic system. The system includes the surgical robotic tool 240 that is depicted in FIG. 2, having one or more tool disks at a proximal end and an end effector at a distal end thereof as shown. A tool drive (e.g., tool drive 230) is mounted at a distal end of a surgical robotic arm 220 as shown, where the tool drive 230 has one or more drive disks 234 each driven by a rotary motor within a housing of the tool drive. Each drive disk 234 is to be attached to a tool disk 244 of the surgical tool 240 to impart motion to the end effector 246.

Staying with FIG. 5C, the process for engaging a tool disk with a drive disk is performed by a control unit, and in particular by one or more processors of the control unit that are configured to (or programmed to) do so. Operation may begin with detecting that the surgical tool is attached to the tool drive (block 582); this may be done by the processor wirelessly or via a wired connection reading an identification or other attributes of the tool, which has been brought into contact with the tool drive such that a tool disk comes into contact with a corresponding or respective drive disk. The control unit may then actuate each drive disk through the rotary motor (block 584), and detect, during the actuation, that a drive disk is engaged to a respective tool disk (block 586); the drive disk is said to be engaged to the tool disk when a pair of coupling features of the drive disk and the tool disk (there may be more than one pair, e.g., two as shown in FIG. 4A-FIG. 4C, or more) become interlocked. To detect the engagement, the control unit recognizes sensed changes in motor status (status of the actuator, or its motor operating parameters), including that a velocity of the rotary motor drops below a predetermined velocity threshold and a torque of the rotary motor rises above a predetermined torque threshold. The velocity threshold may correspond to a velocity at which the motor is substantially stopped, wherein the torque threshold is a value between i) a minimum torque for the motor to overcome the friction between the drive disk and the tool disk before engagement and ii) a maximum torque for the motor to produce. The changes in motor status may be caused by at least one of: the end effector reaching a joint limit, an external force on the end effector, a motion constraint due to another motor of the tool drive being activated, and a combination thereof. Depending on the particular surgical tool, there may be more than one tool disk that is in use for operating the end effector. In that case, the engagement process described above is also performed for each additional tool disk (which has a corresponding drive disk in the tool drive.) The process then continues with block 588 where the control unit signals for example a user interface subsystem of the surgical robotic system to report engagement of the surgical tool but only if all of the tool disks that are in use for the particular tool have been detected as engaged with their respective drive disks.

Figure 6:
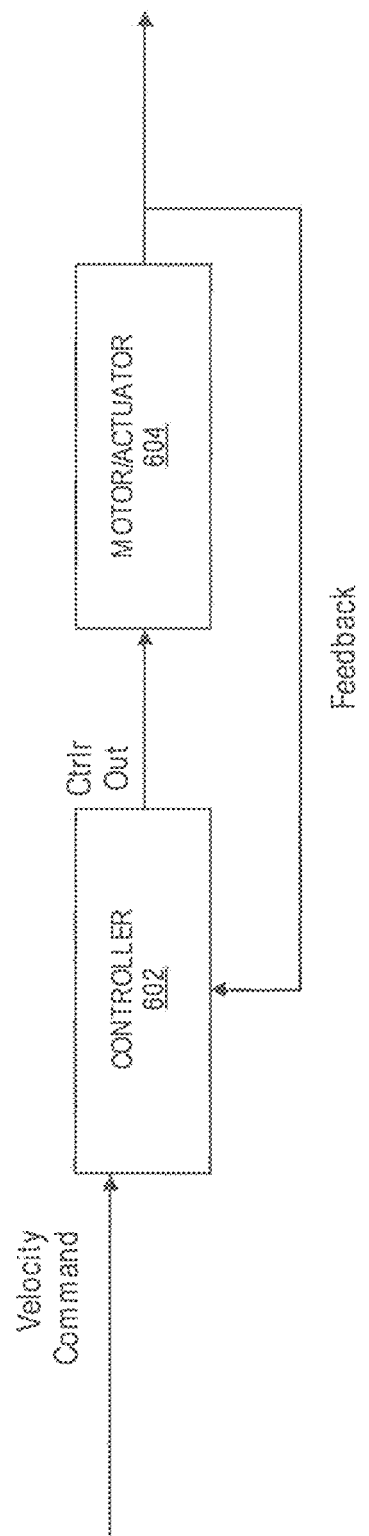
FIG. 6 depicts a block diagram of a feedback loop.

In one embodiment, a feedback loop may be used to monitor one or more motor operating parameters and detect when a threshold has been reached. FIG. 6 depicts a block diagram of a feedback loop used to control the velocity of a motor of a tool drive using velocity feedback. The feedback loop may be implemented in hardware, firmware, software, or a combination thereof. A velocity command is received by a controller 602. Controller 602 may be, for example, a proportional-integral-derivative controller (e.g., PID controller 702 of FIG. 7) providing a loop/feedback mechanism to provide an appropriate motor current (e.g., the controller output, ctrlr out) to drive motor/actuator 604 at the velocity and in the direction of the velocity command (also referred to as velocity setpoint.) For example, the direction may be in a winding direction of a cable driven tool disk 244-j. As another example, the direction may be a direction that will oppose the motion of another motor whose attached tool disk 244-i should be cooperating with the tool disk 244-j. As yet another example, the direction may be a direction that causes the motor to advance the end effector towards a hard stop, such as a physical barrier or a mechanical limit of range of motion. In one embodiment, the controller 602 may use various values, such as desired torque to achieve the velocity, current to achieve the velocity, impedance indicative of a velocity, etc. as a measure for generating the controller's current output to motor/actuator 604.

A sensor, such as a torque sensor, velocity sensor, or a combination of sensors, measures the actual velocity of the motor/actuator. The actual velocity is then provided as feedback back to controller 602, which may calculate an error based on a disparity between the actual velocity of the motor and the commanded velocity. The controller 602 responds to the disparity by adjusting its controller output, e.g., a motor current command to the motor/actuator 604, a torque to be achieved by the motor/actuator 604, an impedance value, etc. that will cause the motor/actuator 604 to move towards the velocity command or setpoint. In some embodiments, controller 602 may output a motor operating parameter, such as the torque, current, impedance, velocity, etc., calculated as a result of executing the feedback loop.

In another embodiment, controller 602 can include a saturation block (not shown) to ensure that the controller output (e.g., a value that is controlling the motor current) does not exceed a threshold, e.g. a current threshold, torque threshold, impedance threshold. The value used by or input to the saturation block may be dual-purposed, namely also used as the motor operating parameter value supplied to the processor (for purposes of being monitored during the engagement process.)

Figure 7:
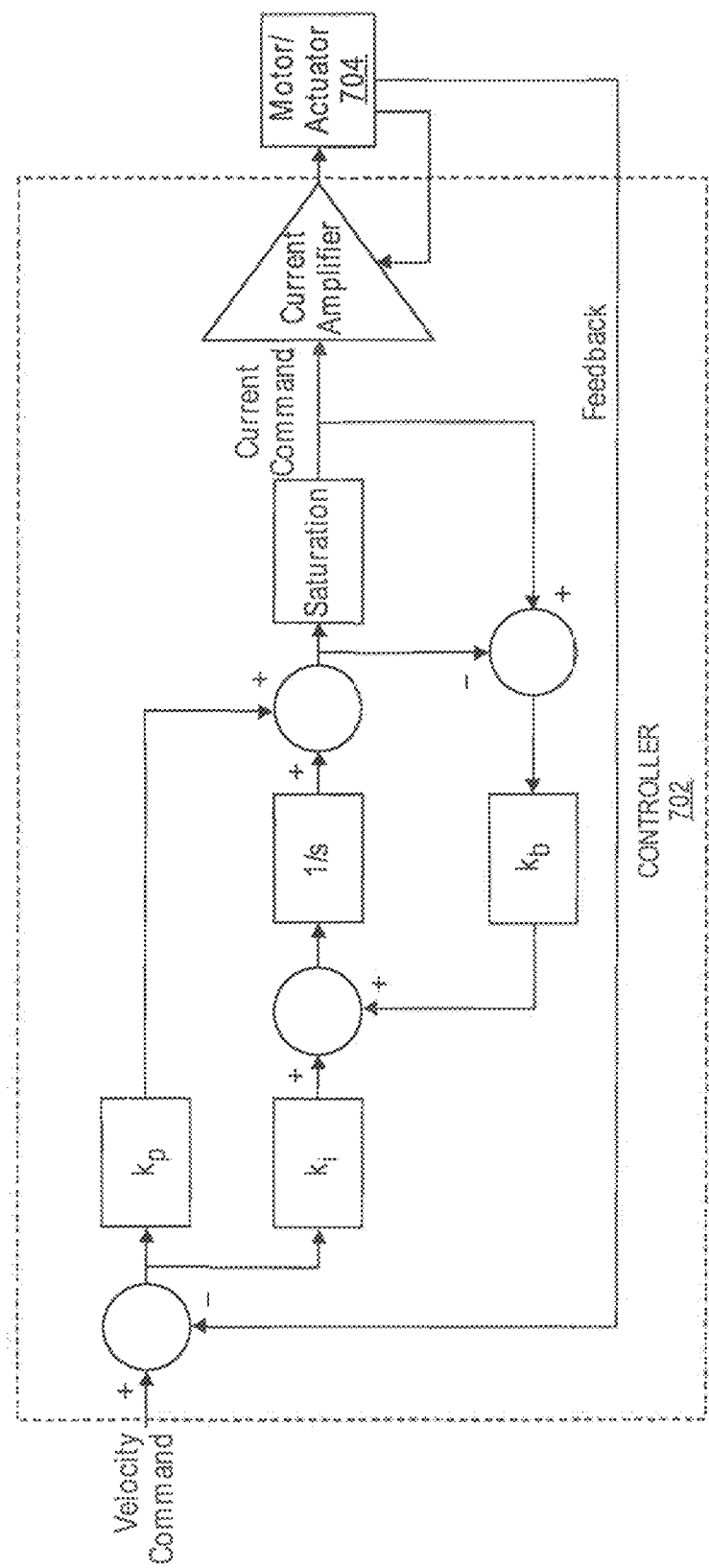
FIG. 7 depicts a block diagram of a controller for use in a feedback loop.

FIG. 7 depicts a block diagram of a feedback loop that includes a controller 702 for controlling the velocity of a motor of a tool drive. In one embodiment, controller 702 is a proportional-integral (PI) controller and may be used within controller 602, and may be implemented in part as hardware, firmware, software, or a combination thereof.

A velocity command (e.g., control variable setpoint) is received by controller 702. Controller 702 provides a loop/feedback mechanism to adjust and provide an appropriate current (e.g., the controller output) to drive motor/actuator 704 at the velocity and in the direction of the velocity command/setpoint. For example, the direction may be in a winding direction of a cable driven surgical tool's tool disk. As another example, the direction may be a direction that will oppose the motion of another motor of the tool drive. As yet another example, the direction may be a direction that causes the motor to advance the end effector towards a hard stop, such as a physical barrier or a mechanical limit of range of motion. In one embodiment, the controller 702 may use various values, such as desired torque to achieve the velocity, current to achieve the velocity, impedance indicative of a velocity, etc. as a measure for generating the controller's current output to motor/actuator 704.

Adjustments are made to the original velocity command, such as a proportional adjustment (e.g., block $k_p$) to adjust the velocity proportional to an error (e.g., as determined by the feedback), as well as an integral adjustment (e.g., block $k_i$) to adjust the velocity to account for past error integrated over time. The integral adjustment may further be adjusted using a restoring term generated by block $k_b$ which is in feedback loop for anti-windup, to further adjust the value of the integral adjustment. The integral adjusted value may be further adjusted by block 1/s (e.g., before being added to the proportional setpoint adjusted value. In one embodiment, a saturation block may be used in controller 702 as shown, to ensure that a value controlling the current supplied to the motor does not exceed a threshold, e.g. a current threshold, torque threshold, impedance threshold, etc. After the adjustments are carried out by the blocks discussed above, and the resulting current command value does not exceed the value set in the saturation block, the current command (e.g., the adjusted command, which has been corrected based on the feedback and PI adjustments) is fed into the current amplifier, so that the commanded current into the motor actuator 704 can be amplified by a factor. The factor may be fixed, based on properties of the motor/actuator 704, based on feedback from the motor/actuator 704, etc. The motor/actuator 704 is activated as per the amplified current, and feedback (e.g., speed, torque, velocity, etc. as determined by a sensor coupled with a motor) on the velocity response of the motor/actuator 704 is provided to the feedback loop implemented by controller 702 as shown.

As discussed above, the value used by (or input to) the saturation block may be used as the motor operating parameter value supplied to the processor for purposes of monitoring during the engagement process, e.g., representing present motor current or present motor impedance.

In another embodiment, the feedback may be used as a motor operating parameter value supplied to the processor for purposes of monitoring during the engagement process. Other variables computed in the controller 702 (e.g., adjusted and non-adjusted) may be used as a monitored motor operating parameter.

In one embodiment discussed above, two actuators share the load in moving a surgical tool, such as sharing the load to rotate an endoscope. The surgical tool (e.g., endoscope) may have a rotation joint without an encoder so the position is determined from the angles of the motors or actuators. Without engagement, the rotation angle of the surgical tool cannot be determined. There is no mechanical hard stop on the rotation joint, so a hard stop may not be used for homing. The rotation joint is coupled with two motors on the tool driver. In normal operation, these two motors are working cooperatively to drive the rotation joint. For example, in teleoperation after engagement and homing, one motor is primary and controlled in position mode, and the other motor is secondary and controlled in position or current (torque) mode. Both motors drive the movement of the surgical tool in the same direction. Before the two motors drive the endoscope rotation joint, the motors have to be both engaged to the rotation joint, and the endoscope joint angle is calculated (i.e., homed) based on motor joint positions upon completion of engaging.

FIG. 2 shows an example surgical robotic system for engagement and/or homing of motor control in a robotic surgery system. In general, two or more drive discs 234 are to engage with a respective two or more tool pads or discs 244. The pads may have other shapes than discs, such as being plus ("+") shaped. The example herein uses discs.

The surgical tool 240 is a surgical tool, such as any of the surgical tools used in medicine or discussed herein. In one embodiment, the surgical tool 240 is an endoscope. Rather than having scissors, clamps, or other tools, the surgical tool 240 has a camera at the distal end as the end effector 246. The endoscope shaft is able to rotate 360 degrees without a hard stop. Any number of rotations may be possible due to there being no hard stop or physical restriction on the rotation. Other tools for rotation or other movements may be used.

The robotic surgical tool 240 includes a housing, a shaft, and an end effector 246 from proximal end to distal end. The tool discs 244 are positioned in the housing and linked to the end effector 246 (e.g., by cable, rod, and/or other transmission), which is driven by the drive discs 234 through the tool discs 244 and transmission after properly engaged.

The rotary tool discs 244 connect to the shaft of the surgical tool 240 for rotating the surgical tool 240. Two or more rotary tool discs 244 connect through a transmission to link the tool discs 244 to the surgical tool 240. Gearing, clutch, cables, belts, and/or other linkages receive force, such as rotational force, from two or more tool discs 244 to rotate the surgical tool 240. The power to rotate the surgical tool is shared. In one embodiment, both tool discs 244 rotating in a same direction both contribute to rotating the surgical tool 240 in the same or an opposite direction. In another embodiment, the transmission links so that two tool discs 244 rotating in opposite directions rotate the surgical tool 240 in one of the directions.

The tool drive 230 includes the actuators 238 (e.g., motors) connected directly or through a transmission to the drive discs 234. The actuators 238 and drive discs 234 form rotatory motor drives, which are mateable (e.g., engaging coupling features 447 and 448) with the tool discs 244. The drive discs 234 mate with the tool discs 244. The engagement or mating occurs once the surgical tool 240 is connected to the tool drive 230.

The sensors 236 are one or more different sensors. For example, the sensors 236 are encoders for detecting position, such as angular position, of the motor shaft and/or drive discs 234. The encoder may output position information so that a processor may determine a velocity from a time derivative of position. As another example, the sensors 236 are current sensors (e.g., current sensing resistor in series with a motor input drive terminal) for detection of the amplitude of the current provided to and/or drawn by the actuators 238. Additional, different, or fewer sensors 236 may be provided for each actuator 238, such as providing both current sensors and encoders.

Figure 9:
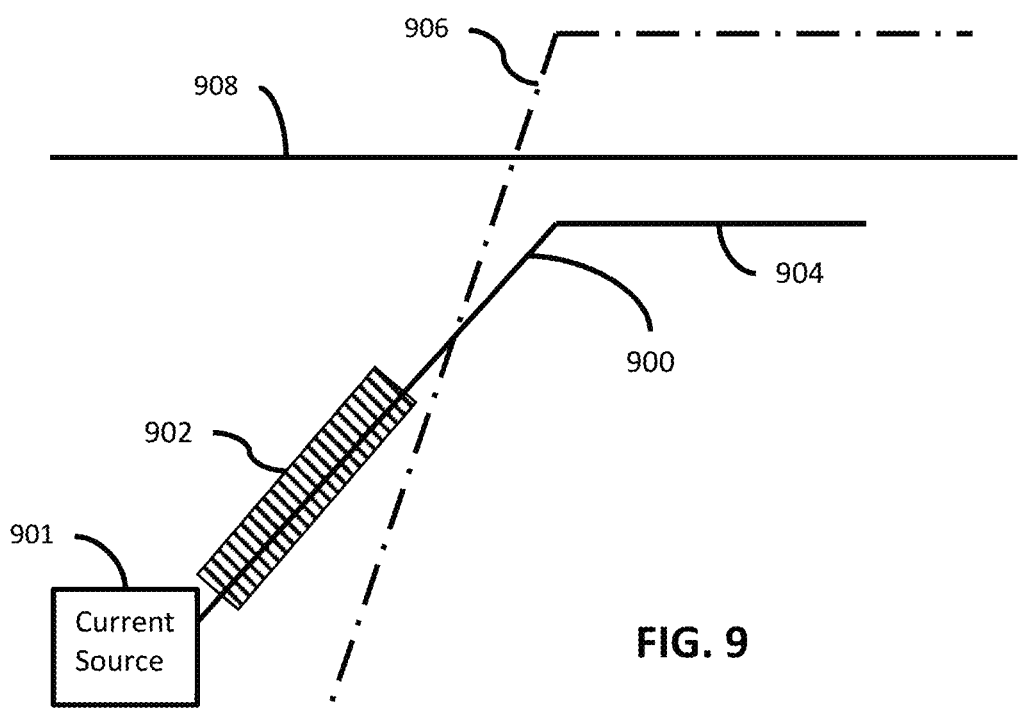
FIG. 9 illustrates one embodiment of a drive current used for engagement.

As shown in FIG. 9, a current source 901 may be provided. The current source 901 outputs current to the actuator 238. Based on control signals, the current source 901 provides current to move the actuators 238 in position, torque (e.g., current) or other modes of control. The actuators 238 are supplied with current to cause rotation to given angular positions (position mode) or to move at a given velocity (e.g., current mode). Other control modes may be used.

In one embodiment shown in FIG. 9, the current source 901 adds a dithering current 902, such as high frequency (e.g., 60 Hz or higher (e.g., 100 Hz)) sinusoidal current. The dithering current 902 is low amplitude, such as being 10% or less of a maximum current 908. The dithering current 902 is added to a ramp-up current 900 provided to the actuator 238. The dithering current 902 is added during an initial part of the ramp-up current and removed for completion of the ramping. In other embodiments, the dithering current 902 is added over other ranges, such as added after initiating the ramp up current and/or removed after reaching a steady state current 904. The dithering current 902 may assist in reducing static friction during contact between the tool discs 244 and the drive discs 234 for engaging.

The processor 312 of the control unit 210 is configured to detect mating of the rotary tool discs 244 with the respective rotary drives (e.g., rotatory drive discs 234) by a change in a signal. The engagement of the drive discs 234 with the tool discs 244 is detected. The drive discs 234 under power from the motor or actuators 238 may slide relative to the tool discs 244 until engaged, at which point the tool and drive discs 234, 244 rotate together.

The processor 312 is configured to detect the mating from a change in signal or performance of the actuator 238. The signal from the sensor 236, such as the current and/or velocity, are used to detect engagement. Once engaged, the signal changes. For example, the velocity drops to zero or below a threshold velocity. As another example, the current spikes or exceeds a threshold current. In another example, both the low velocity and current spike are detected as representing engagement or mating.

Since two or more actuators 238 drive the surgical tool 240 in combination, the change in signal for detecting the engagement may be performed for both motor drives. For example, the current and/or velocity for each actuator 238 is monitored to detect mating. The mating for each actuator 238 to the surgical tool 240 is detected.

Where no hard stop is provided, the actuators 238 may be driven in opposition to each other. The motor drives may attempt to rotate the surgical tool 240 in opposite directions and/or at different speeds, opposing each other rather than attempting to rotate together. Each actuator 238 is to drive the surgical tool 240. By operating in opposition to each other, the actuators 238 may attempt to rotate the surgical tool 240 in opposite directions and/or at different speeds. The driving is in position control mode, but current or other modes of control may be used.

When the initial drive disc 234 mates with the corresponding tool disc 244, the signal for that actuator or drive motor may not change much as this initial drive disc 234 is the only drive rotating the tool. The current and/or velocity may change due to the resistance in rotating the surgical tool 240, but the velocity may not change to below the velocity threshold and/or the current may not spike to be above the current threshold. Once the other or later drive disc 235 mates with the corresponding tool disc 244, the two motor drives are both engaged and attempting to rotate the surgical tool 240 in opposite directions and/or at different speeds. As a result, the velocities for both motors drop below the threshold and/or the currents for both motors spike. The motor drives resist each other, acting as mutual hard or soft stops. If the motors have equal strength or power and are rotating at a same speed in opposition to each other, then the velocity drops to zero and the current spikes to the maximum. Where the motors have different power due to design or tolerance and/or different speeds, a greater velocity and/or lesser current spike may be provided while still being below the velocity threshold and/or above the current threshold, respectively.

The processor 312 is configured to verify the engagement. After mating is detected, the engagement may be verified. The encoders indicate the rotational position of the tool discs 244 once engaged. Since the tool discs 244 link to the same surgical tool 240, the tool discs have a known relative rotation with respect to each other. For example, the tool discs 244 are designed to have the same angle but opposite sign for any given rotational position of the surgical tool 240. In other examples, any relative combination of angles may be used. Due to the engagement, the position of the drive discs 234 corresponds to the position of the tool discs 244. Where the angles at engagement match the designed angles, engagement is verified.

Figure 8:
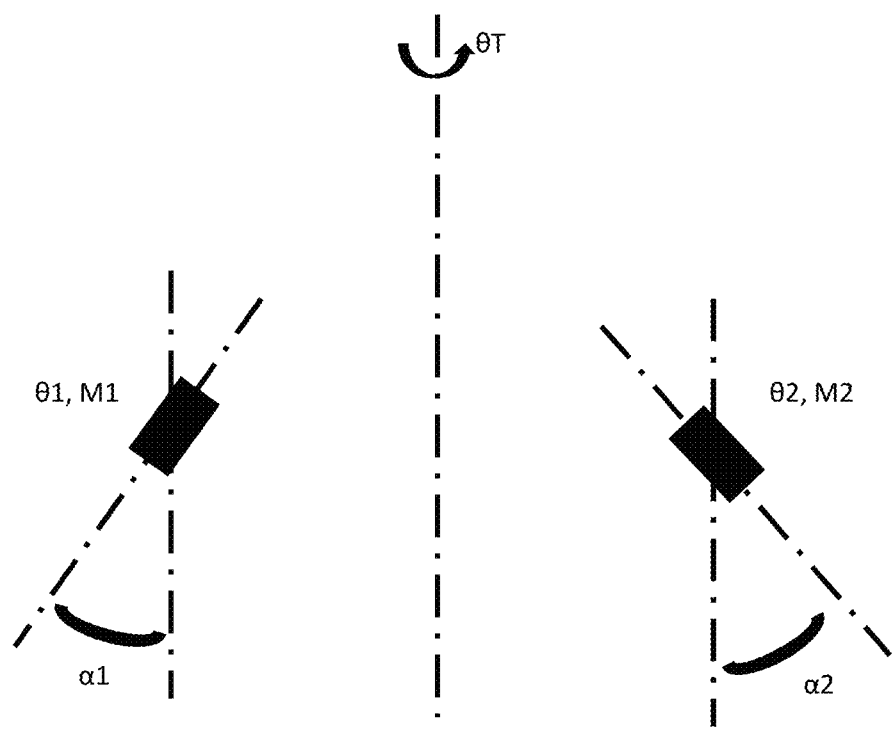
FIG. 8 illustrates an example of the rotational angle relationships between motors and corresponding drive discs, tool discs, and a surgical tool.

The processor 312 is configured to home the rotational angle of the surgical tool 240. The current rotational angle of the surgical tool 240 is determined once engaged. The surgical tool 240 is calibrated so that the angles of the rotatory tool discs 244 for each rotational angle of the surgical tool 240 are known. Upon engagement, the processor 312 determines the rotational angle of the surgical tool based on the rotational angles of the engaged rotary drives (e.g., actuators 238, drive discs 234, and/or tool discs 244) as mated. The calibration relates the angles of the engaged rotary drives to the angle of the surgical tool 240. Referring to FIG. 8, upon completion of engaging, the joint (e.g., tool disc) angles are α1, and α2 respectively when the surgical tool (e.g., endoscope) is at home (zero) position, θT. Both α1 and α2 are pre-calibrated and are measured from the encoder based angles θ1 and θ2 of two motors M1, M2.

FIGS. 8 and 9 shows another embodiment of detection of engagement for two motor drives working to control the same movement of the surgical tool 240. A combination of position and current control modes are used to detect the mating from the change in the signal.

The kinematic equation of motion after the engaging may be represented as:

$$\theta = \gamma * (\theta1 - \alpha1)\theta1 - \alpha1 = -(\theta2 - \alpha2) \text{ where, } \theta, \theta1,$$

$$\theta2 - \text{angles of endoscope joint, motor } M1 \text{ joint},$$

$$\text{motor } M2 \text{ joint } \gamma - \text{gear ratio} \alpha1, \alpha2 - \text{angles of } M1,$$

$$M2 \text{ joints at endoscope zero position}$$

This kinematic equation may be used in engagement detection and/or homing.

In a first step, the motor M2 is set to operation in the position control mode. The target position is set to be the current position, so the motor M2 is held steady or in the current location.

In a second step, the motor M1 is set to operation in a current control mode. As shown in FIG. 9, the current 900 is ramped up until the velocity reaches a threshold, represented by the horizontal portion 904 of the current 900. The offset from the maximum current 908 for the horizontal portion 904 and the slope of the ramp-up may be experimentally determined.

A dithering current 902 is added to the current 900. For example, a high frequency (e.g., 100 Hz) sinusoidal current provides low amplitude dithering and is superimposed on to the ramp-up current. This high frequency current helps to overcome the static friction between the discs 234, 244. The angular velocity 906 of the actuator 238 and drive disc 234 ramps up and then holds steady based on this current control. The direction of the current command (i.e., rotation direction) is arbitrary. The maximum current limit 908 is set between the maximum current to drive the motor alone and the minimum current to drive the coupled motor and endoscope. The limit may be experimentally determined.

During this second step, the engagement for the motor M1 is detected. Engagement is detected where the motor M1 never moves—the current command ramps up to the maximum current. This may occur where the tool disc 244 mates to the drive disc 234 upon connection or placement in contact. Engagement is detected where motor M1 stops before reaching the desired velocity or after reaching the desired velocity. If the motor M1 does not stop after a full rotation detected by an encoder, then the velocity limit may be reduced (e.g., by ½) and the second step is repeated. If the second step fails to detect engagement again, then an error is reported and the process stopped.

In a third step, the motor M1 is set to position mode, and the target position is set to the current position, θ1, to hold the motor M1 in place. In a fourth step, the motor M2 is set to be in current control mode. The same current profile used in the second step (see FIG. 9) is used. The direction of rotation for the current is set to be in the shorter direction towards −(θ1−α1)+α2. The same velocity and/or motion conditions are used to determine whether engagement occurs for the motor M2.

In the second and fourth steps, instead of checking for stops, velocity change may be used to detect engaging status. Once the engagement is confirmed, the current command is set to zero immediately and proceeds to the next step.

Velocity close-loop control with current saturation may be used to replace the current ramp up control in the second and fourth steps. In the second step, the motor M1 is set to velocity control mode, and the target velocity is set to a predefined value. The direction of the velocity is chosen arbitrarily. The engagement status is detected where the motor M1 stops or there is a sudden jump in motor current measurement. In the fourth step, the motor M2 is set in velocity control mode, and the target velocity is set to a predefined value. The direction of the velocity is in the shorter distance to −(θ1−α1)+α2.

In a fifth step, the motor M1 stays in position control mode, and the motor M2 stays in the current control mode. The joint angles of motors M1 and M2 are checked to verify that the kinematic equation is satisfied. Complete engagement is confirmed where the angles match to design angles. If engaging fails twice in a row and/or the verification fails, then the engagement process may be stopped and an error reported.

After successful engaging, homing may be established. The endoscope joint angle relative the zero position may be calculated from the motor M1 joint angle using the kinematic equation.

Figure 10:
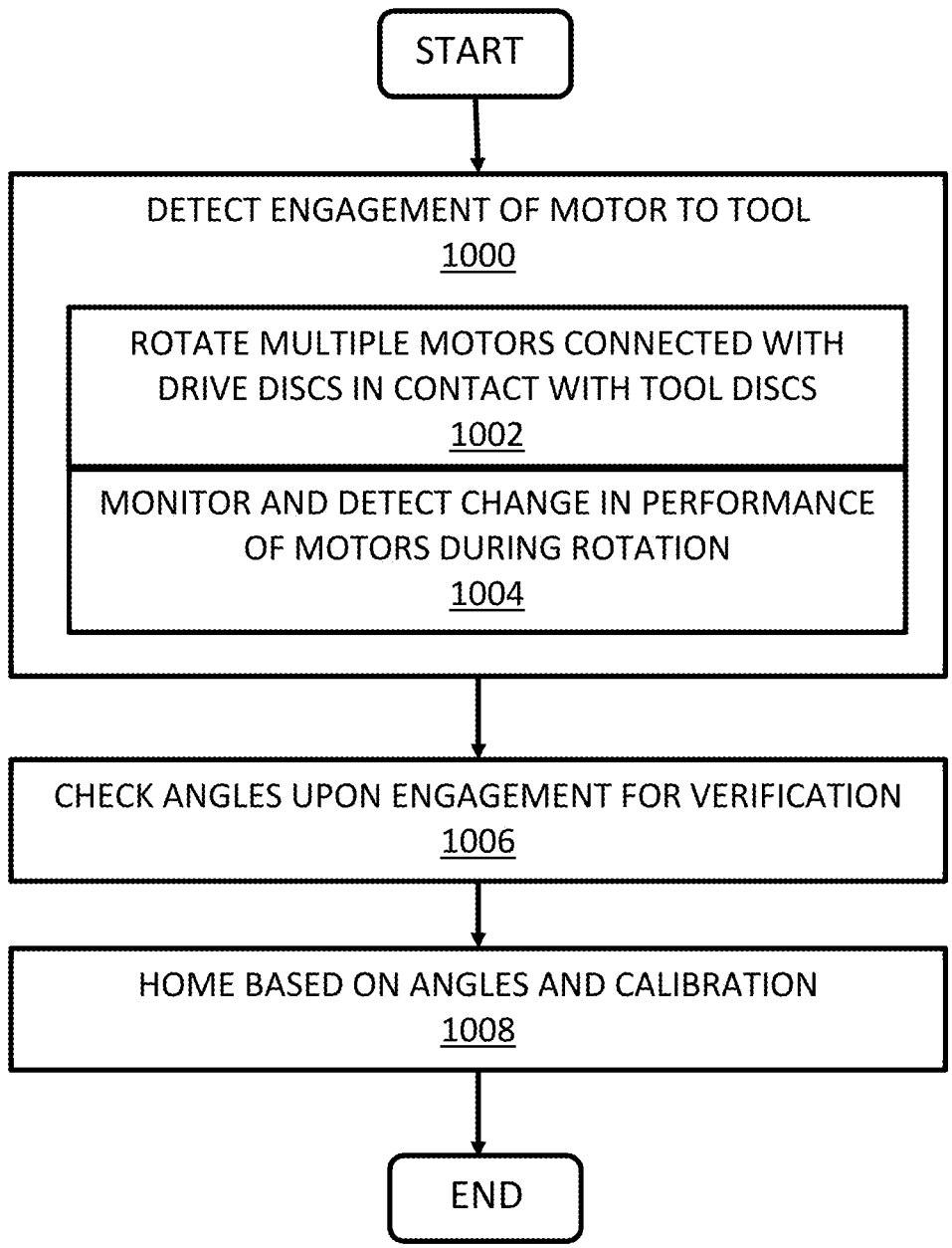
FIG. 10 is a flow diagram illustrating another process for a control unit detecting engagement and/or for homing.

FIG. 10 shows one embodiment of a method for engaging motor control of a surgical tool in a surgical robotic system. The method also includes homing a rotational position of a surgical tool in the surgical robotic system. For example, engagement of an endoscope with tool driver motors (M1, M2) and/or homing are provided. Engaging drives the motors until both motor joint shafts are securely coupled with the endoscope shaft through key and/or key hole or another coupling. Homing finds a joint angle between the zero position of the endoscope rotation joint and the primary joint encoder position.

The method is performed by the surgical robotic system of FIGS. 2 and 3 or another surgical robotic system. The method is performed where two motors drive the same motion of the surgical tool, such as rotation in a same direction by an endoscope. A processor of the control unit or other controller performs the method upon connecting the surgical tool 240 to the tool drive 230. Once the identity of the surgical tool 240 is determined as one with two or more motors combining power or motion to drive the same movement, the processor performs the engagement detection and/or homing.

The acts are performed in the order shown or a different order. For example, acts 1002 and 1004 are performed simultaneously. As another example, acts 1002 and 1004 are repeated to detect engagement of different motors. Additional, different, or fewer acts may be provided. For example, acts 1006 and/or 1008 are not provided for detection of engagement. As another example, acts 1002 and 1004 are not provided where other engagement detection is used. In yet another example, act 1006 is not provided. In other examples, acts for teleoperation or surgical use of the engaged and homed endoscope or another surgical tool are provided. In one embodiment, the attachment of the surgical tool to the tool drive is detected (see acts 552 of FIG. 5B and 582 of FIG. 5C) to then trigger detection of engagement f the discs.

In act 1000, the processor (e.g., controller or control unit) detects engagement of two or more rotary tool pads or discs 244 with a respective two or more rotary drives (e.g., actuators 238 and drive pads or discs 234). Using releasable (e.g., spring loaded, physical barrier, or friction fit) fittings, the drive discs 234 mate with the tool discs 244.

In act 1002, the motors (e.g., actuators 238) rotate. The rotation of the motors is performed under position control, but other control modes may be used. During teleoperation to rotate or translate the surgical tool in one direction, the two motors rotate in specific directions (e.g., both motors rotate in the same direction or one more rotates in one direction and another motor rotates in a different direction), depending on the transmission or other linkage from the tool discs 244 to the surgical tool 240. For engagement, the motors rotate in opposition to each other. For example, an endoscope is rotated clockwise by rotating one motor clockwise and the other motor counterclockwise. To rotate in opposition to each other, the motors rotate in the same direction so that one motor attempts to rotate the endoscope clockwise and the other attempts to rotate the endoscope counterclockwise. Since the endoscope is free of a hard stop or physical limiter to rotation, the opposition rotation of the motors that share movement burden resist each other, acting as stops once engaged.

Due to the motor rotation, the drive discs 234 connected to the motors directly or through gearing rotate. The drive discs 234 are in frictional contact with the tool discs 244. The rotation has sufficient force to overcome static friction, so the drive discs 234 rotate relative to the tool discs 244, which are linked to the surgical tool (e.g., surgical tool 240 or endoscope). The rotation should eventually result in engagement of the physical engagement mechanism (e.g., protrusion and indent, shaped extension and slot, protrusion and stop, and/or snap fit holder and extension) on the tool and drive discs 234, 244.

Dithering in current, position, and/or other control modes may be used. By dithering the command signal, static friction may be more easily overcome so that the drive disc 234 rotates at a greater rate than the tool disc 244 for engagement.

Once both or multiple pairs of tool and drive discs 234, 244 are mated or engaged, then the rotation in opposition acts as a stop. Once engaged, the force of rotation from each motor transfers through the linkage or transmission linking the tool discs 234, causing resistance in movement.

In an alternative embodiment, one of the motors is controlled in position mode to not rotate while the other motor rotates to engage. Once one motor is engaged, the engaged motor drive does not rotate while the other motor engages. For example, the steps described above with reference to FIG. 9 are performed.

In act 1004, the processor (e.g., control unit or controller) monitors for and detects engagement of the motors (e.g., actuators 238) with the respective tool discs 244. The detection is based on monitoring for a change in performance of the motors. The change may be represented as a difference, such as a difference in performance above a threshold (e.g., current doubled or increased by over X amount). The change may be represented as an absolute value relative to a threshold, such as the velocity transitioning to below a threshold velocity (e.g., velocity going to zero) and/or the current transitioning to be above a threshold (e.g., current spiking).

Once the performance change using one or more parameters (e.g., both current and velocity) for each of the motors occurs, then engagement is detected. Engagement may be detected as engagement by all or a sub-set of the motors. Once the performance characteristic of each of the motors or each of the sub-set of motors changes, engagement of the surgical tool is detected. Alternatively, engagement is detected separately for each motor. Once all the desired motors are engaged, the engagement process ends.

In act 1006, the processor (e.g., controller or control unit) checks or verifies engagement. Once engagement is detected, a check is performed to verify proper engagement. The check relies on the transmission or linkage between the tool discs 244 and the surgical tool 240. Since both tool discs 244 drive the same motion, the angle of the tool discs 244 to each other is fixed or within a tolerance range. The mechanism for engaging has a fixed orientation on the tool discs 244 and drive discs 234, so the engaged tool discs 244 have that fixed orientation where both are engaged. The angles of the drive discs 234 and corresponding motor shafts are measured by the sensor 236 (e.g., encoder). Due to engagement, the angles correspond to the angles of the tool discs 244.

The angles of rotation are compared. Where the expected angles or angles of rotation within a threshold are detected, the engagement is verified. For example, the transmission or linkage between the tool discs 244 is designed to have the same angle with opposite signs for any rotational position of the surgical tool 240 (e.g., endoscope). Once engaged, the rotatory position of the motors and drive discs 234 have the same angle (e.g., same absolute angle with different signs). Other angle combinations may be used.

In act 1008, the processor (e.g., controller or control unit) determines a current rotation angle of the surgical tool once engaged. This homing determines a rotation angle of the medical instrument upon the engagement.

The rotation angle is determined from the angles of the motors and respective drive discs 234. Once engaged, the angles of the drive discs 234 from the sensors 236 are the angles of the tool discs 244. A look-up table or other function from calibration maps the angles of the tool discs 244 (and/or drive discs 234) to the angle of the surgical tool. The transmission relates the tool disc 244 angles to the surgical tool angle or position, and the calibration measures the relationship. Once the angles for the discs 234, 244 for each of the motor drives is determined, the calibration is used to find the angle of the surgical tool 240.

The engagement and/or homing process then ends. If engagement is not detected in act 1000, engagement is not verified in the check of act 1006, and/or homing of act 1008 fails, the process for engagement is repeated or a different engagement process may be performed. If multiple failures occur, then an error message is sent. Where engagement and/or homing are performed successfully, then the surgical tool 240 and motor drives are ready for teleoperation in surgery.

The above description of illustrated embodiments of the invention, including what is described below in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize. For example, although FIG. 4A-FIG. 4C depict a surgical tool 240 that has a cable-driven transmission connecting the tool disk 244 to the end effectors (not shown), the engagement process described above is also applicable to other types of surgical tools having different transmissions (not necessarily cable-driven.) These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method for tool engagement in a surgical robotic system, the method comprising:
    detecting a mechanical attachment of a surgical tool to a tool drive, the tool having a first tool disc and a second tool disc to be engaged with a first drive disc and a second drive disc, respectively, of the tool drive, the first and second tool discs linked to an end effector of the surgical tool;
    actuating the first drive disc by a first motor and the second drive disc by a second motor of the tool drive such that the first and the second drive discs rotate in opposition to each other;
    monitoring performance of the first and the second motors; and
    detecting engagement of the first and second tool discs with the first and second drive discs based on changes in the performance of the first and second motors.

2. The method of claim 1 wherein actuating comprises actuating the first and second drive discs, by the first and second motors, with position control mode.

3. The method of claim 1 wherein actuating the first and second drive discs comprises the first and second motors actuating in a same direction where a link between the first and second tool discs to the end effector uses rotation of the first and second tool discs in opposite directions to rotate the end effector in a same direction.

4. The method of claim 1 wherein movement of the end effector of the surgical tool comprises rotation of an endoscope free of a hard stop.

5. The method of claim 1 wherein detecting engagement comprises detecting spikes in currents to the first and second motors.

6. The method of claim 1 wherein detecting engagement comprises detecting first and second velocities below a velocity threshold of the first and second motors, respectively.

7. The method of claim 1 wherein detecting engagement comprises detecting first and second velocities of the first and second motors, respectively, being within a threshold amount of zero.

8. The method of claim 1 further comprising applying a dithering current to a current ramp in current control mode to the first motor, wherein detecting engagement is based on changes in the performance of the first motor while in the current control mode.

9. A surgical robotic system comprising:
    a tool drive having a first drive disc and a second drive disc; and
    a processor configured to
        detect a mechanical attachment of a surgical tool to the tool drive, the surgical tool having a first tool disc and a second tool disc to be engaged with the first drive disc and the second drive disc, respectively, the first and second tool discs linked to an end effector of the surgical tool,
        signal a first motor of the tool drive to actuate the first drive disc, and a second motor of the tool drive to actuate the second drive disc, so that the first and the second drive discs rotate in opposition to each other,
        monitor performance of the first and the second motors while the first drive disc and the second drive are actuated, and
        detect engagement of the first and second tool discs with the first and second drive discs based on changes in the performance of the first and second motors.

10. The system of claim 9 wherein the processor signals the first and second motors to actuate the first and second drive discs in position control mode.

11. The system of claim 9 wherein the processor signals the first and second motors to actuate in a same direction, and the link in the surgical tool uses rotation of the first and second tool discs in opposite directions to rotate the end effector in the surgical tool in a same direction.

12. The system of claim 11 wherein movement of the end effector comprises rotation of an endoscope free of a hard stop.

13. The system of claim 9 wherein the processor is to detect engagement by detecting spikes in currents to the first and second motors.

14. The system of claim 13 wherein the processor is to detect engagement by detecting first and second velocities below a velocity threshold of the first and second motors, respectively.

15. The system of claim 13 wherein the processor is to detect engagement by detecting the first and second velocities of the first and second motors, respectively, being within a threshold amount of zero.

16. The system of claim 9 wherein the processor is configured to apply a dithering current to a current ramp in current control mode to the first motor, and detect engagement based on changes in the performance of the first motor while in the current control mode.

* * * * *